(12) United States Patent  
Solomon

(10) Patent No.: US 8,172,724 B2  
(45) Date of Patent: May 8, 2012

(54) COMPUTER AUTOMATED PHYSICAL FITNESS SYSTEM

(75) Inventor: Neal Solomon, Oakland, CA (US)

(73) Assignee: Neal Solomon, Oakland, CA (US)

( * ) Notice: Subject to any disclaimer, the term of this patent is extended or adjusted under 35 U.S.C. 154(b) by 0 days.

(21) Appl. No.: 12/932,047

(22) Filed: Feb. 16, 2011

(65) Prior Publication Data

US 2011/0201476 A1 Aug. 18, 2011

Related U.S. Application Data

(60) Provisional application No. 61/338,250, filed on Feb. 16, 2010.

(51) Int. Cl.
*A63B 71/00* (2006.01)

(52) U.S. Cl. ............ 482/8; 482/1; 482/9; 482/901

(58) Field of Classification Search ............ 482/1–9, 482/900–902; 434/247
See application file for complete search history.

(56) References Cited

U.S. PATENT DOCUMENTS

| | | | |
|---|---|---|---|
| 7,473,211 B2* | 1/2009 | Lee | 482/97 |
| 2009/0221404 A1* | 9/2009 | Dorogusker et al. | 482/8 |
| 2010/0298097 A1* | 11/2010 | Preumont et al. | 482/5 |

* cited by examiner

*Primary Examiner* — Glenn Richman

(57) ABSTRACT

The invention provides a system for organizing, integrating, coordinating and customizing an individual physical fitness program by employing a set of database management systems, computer platforms and differentiated physical fitness devices and components.

18 Claims, 18 Drawing Sheets

FIG. 17
(I)
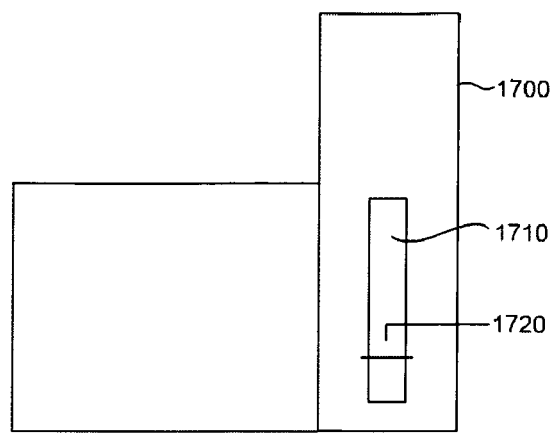
(II)
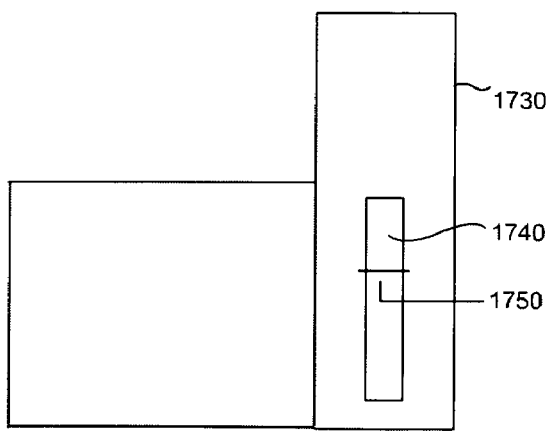
(III)
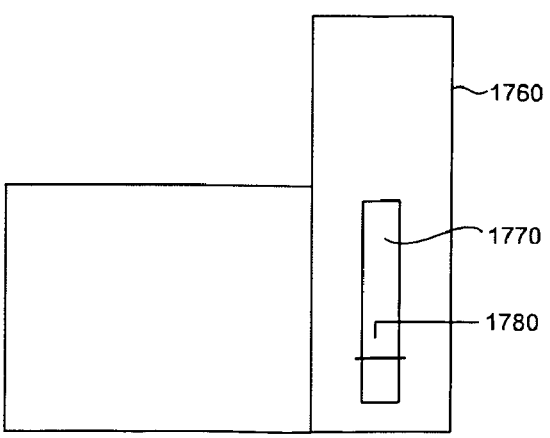

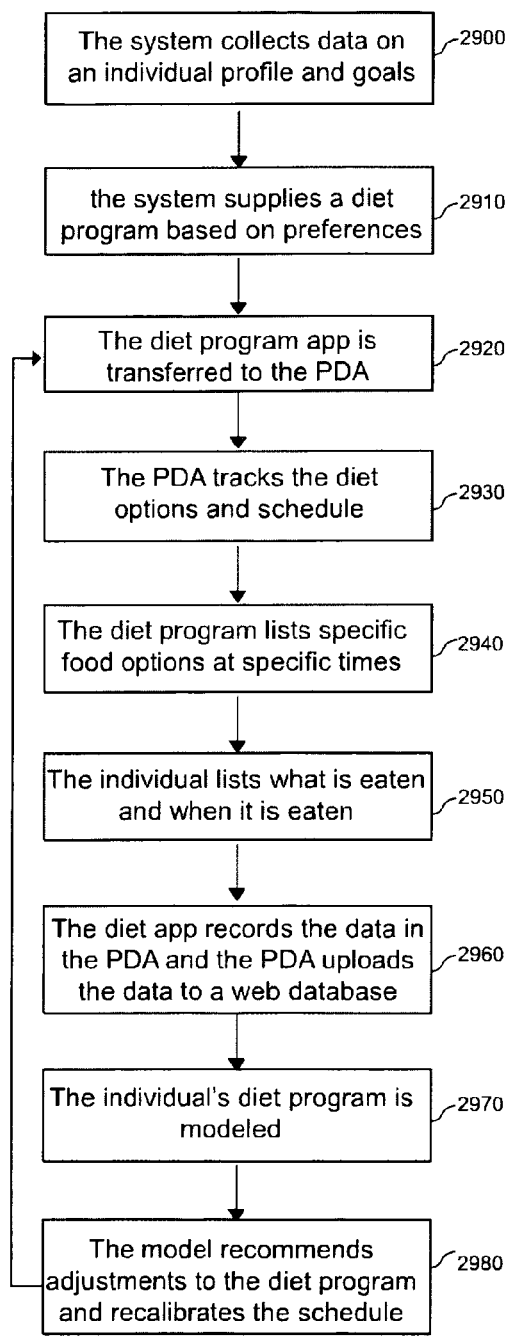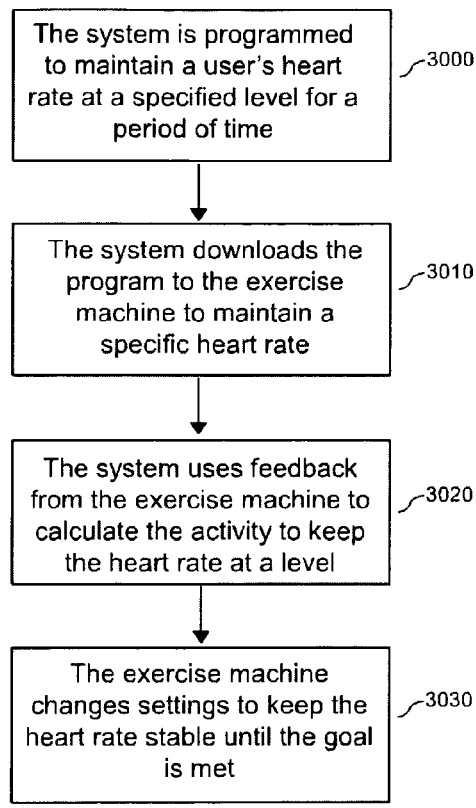

COMPUTER AUTOMATED PHYSICAL FITNESS SYSTEM

CROSS-REFERENCES TO RELATED APPLICATIONS

The present application claims the benefit of priority under 35 U.S.C. §119 from U.S. Provisional Patent Application Ser. No. 61/338,250, filed Feb. 16, 2010, the disclosure of which is hereby incorporated by reference in their entirety for all purposes.

FIELD OF INVENTION

The present invention involves multi-platform database management systems applied to physical fitness optimization processes. The system utilizes multi-functional computer program code to solve evolutionary multi-objective optimization problems relating to customized fitness.

BACKGROUND OF THE INVENTION

Scientific evidence has established that exercise is known to improve and maximize individual health and to constrain the effects of aging. One of the best ways to achieve a work out is to use gymnasiums that contain a set of exercise machines. However, gym equipment is static and requires a user to manually set each function.

In the best case, an individual will work with a personal trainer in order to obtain the benefits of experience and customization of a workout for a particular individual. However, using a personal trainer and a gym with extensive equipment is expensive. Further, while a personal trainer is useful in some cases, each trainer's knowledge varies and the end experience is random regarding achieving the preferred effects of a customized workout.

Problems with Existing Technologies

The problems with manual and static exercise equipment include:
(a) How to organize a workout?
(b) How to develop an active system for consolidating aspects of a workout?
(c) How to develop an integrated system that coordinates with each machine at the gym?
(d) How to integrate computers and communications into an efficient fitness system?
(e) How to integrate and use database management systems into an efficient fitness system?
(f) How to integrate software programming components into an efficient fitness system?
(g) How to offer access to information on-demand before, during and after a workout?
(h) How to track, assess, analyze and model data on an individual workout?

While there are specific approaches used to address a single aspect of a complete approach to physical fitness, none come close to providing an integrated solution to the problem of optimizing an individual workout. Fitlinxx, for example, offers a computerized tracking system within some specific weight machines to count repetitions. Also, "PT on the Net" provides a simple approach to enable an individual to track an aerobic workout. Pocketgear provides a personal digital assistant application to track elements of an individual workout. Aerobic equipment (e.g., Stairmaster or elliptical equipment) generally uses preset protocols of common exercise routines. Finally, personal trainers use personal digital assistants (PDAs) and apps to manually track client behaviors in a gym with general data such as machine type, weight setting and number of reps.

These prior approaches are generally pre-programmed and simplistic uses of existing machines. However, all of these and similar approaches are passive; they involve manually setting and recording data to obtain parts of a workout. None of these approaches involve a complete, automated and coordinated workout that customizes an individual's fitness, anticipates appropriate corrections and analyzes optimal exercise processes. None of these approaches provides a systematic approach that includes modeling an individual's workout to accommodate preferences. Finally, none of these approaches provides a system for cross-platform performance including gym equipment of different types, a PDA, multiple apps, a computer, a web component and Web database components.

SUMMARY OF THE INVENTION

In order for individuals to maximize their health, many health experts suggest that they eat a balanced diet, take health supplements and exercise. Though the best exercise will vary for each individual, the best fit individuals will obtain weight (i.e., strength) training, endurance training, aerobic (i.e., cardio) training and flexibility training. So far, an individual-centered health activity system does not exist. What is needed is an automated, integrated and customized exercise regimen tailored to each individual.

The advent of a new paradigm in computing technologies makes possible the development of an automated, integrated and customized fitness system. The use of different specialized exercise machines, a PDA (e.g., tablet or smartphone), PDA software applications, a computer, computer programs, the Web and cloud computing makes possible a new generation of automated fitness system that comes closer to the goal of personalization. The present a system allows individual fitness data to be organized, integrated and analyzed to accommodate interaction and feedback in order to continually optimize the fitness regimen for each individual. The interactive and modeling components of the integrated automated multi-platform fitness system satisfy the goal of a complete personalized workout. The system includes an information component, an active service component and an analytical and advisory component. The present invention advances this goal.

By using this customized automated fitness system, fitness training becomes automated (with no need for expensive personal trainers), with more individual control and more information, with the ability to track, analyze and model physical experiences with recommendations for individual improvements, and, finally, with feedback and constant workout optimization.

The system begins with an assessment of an individual situation, requirements and goals. From the initial individual assessment the system generates recommended exercises. The exercise program is organized as a series of sequences of weight equipment and aerobic equipment procedures. Once the exercise program is executed by an individual, the system sets and tracks the specific exercise machine programs to match their specific requirements. Each exercise session program is evaluated. Recommendations are made from this analysis and the exercise program is modified to optimize each individual's performance. In addition, preferred options for each exercise are input to accommodate individual preferences.

Novelties of the Invention

The invention contains a set of novelties over earlier approaches. First, the system automates a workout on multiple exercise machine types. Second, the system allows each individual to customize their workout to their own, and evolving, specifications. Third, the system allows a continuously optimizing workout so as to promote high performance. Next, the recording, storing, tracking and analyzing of individual exercise data is an advance over earlier approaches. Additionally, the present invention integrates multiple computer platforms to facilitate system processes. Further, the present system provides recommendations to individuals to improve workout exercises from modeling. Finally, the system automatically adjusts fitness equipment programming and configuration to integrate into personalized training processes.

Advantages of the Invention

The invention has numerous advantages. First, the use of automation applied to a range of fitness machines and processes leads to a more efficient workout. Second, increased workout efficiency leads to lower costs of obtaining a workout, which means that gyms can cut their costs and remain more economically competitive. Third, a customized workout for each individual maximizes exercise benefits. Next, the ability for the system to automatically track exercise data allows a third-party, such as a physician, to analyze and modify the program regimen (viz., remotely and in real-time) so as to maximize an individual's health. Finally, the constant modulation of a workout for individual performance improvement or for dealing with an injury can be achieved by using the system.

SUMMARY OF THE PREFERRED EMBODIMENTS

The present invention is divided into four main parts: (I) Personal Digital Assistant and PDA Applications; (II) Exercise Machines; (III) Free Motion Sensor System; (IV) Database Management Systems and; (V) Modeling and Analytics. In addition to these main system components, the present invention describes three specific embodiments.

(I) Personal Digital Assistants

PDAS (such as tablet computers and smart phones) are becoming increasingly ubiquitous because of their usefulness and wireless access to the Web. For the purposes here, the PDA, tablet and smartphone are used interchangeably. A PDA may be a tablet computer. The PDA may have, but does not require, a touch screen. PDAs will typically contain a GPS chip to track the location of the user. PDAs use software applications to perform specific functions.

(A) PDA Applications

Though there are thousands of smart phone and PDA apps, so far most apps only supply information from a Web site or allow data to be input manually.

The present invention uses PDAs and apps in novel ways. When enabled with advanced apps, the PDA is an active intermediary device connecting the exercise machine and the Web-based database. The PDA is also an interface with the individual, allowing information in real-time to be registered and transmitted.

Specifically, the PDA tracks and interacts with exercise machine sensors to collect data on an individual's workout. The PDA accesses data wirelessly and records the data on an individual's workout from each machine.

Specific software apps are downloaded to the PDA either from a computer that accesses a Web site program or directly from a Web site.

PDA apps use exercise programs that are based on a general typology of exercise regimens. Different main exercise program types are organized in a database for selection by each user.

Individual users are able to select specialized PDA apps to suit their preferences. In addition to exercise programs, these include functionality for heart rate monitoring, specific programs for specific cardio machines (e.g. elliptical devices, stationary bicycles, step masters, treadmills, etc.), calorie counting functions and new features of exercise programs. These specific features are downloaded in real time upon request. These specialized apps add more functionality to the system. Further, third-party apps are used to add increased functionality.

(B) Personalized Apps

In addition to traditional apps used to track a workout, individual users are able to select apps that are personalized to their workout. The customized apps are comprised of multiple features that supply an individual-centered workout with PDA assistance. In general, these customized apps emulate a personal trainer by using a personalized exercise program that matches each individual to specific weight and cardio exercise machines. Once the customized exercise program is implemented, each exercise machine activates sensors and actuators to perform specific functions. For instance, for weight machines, each prospective weight level is identified and maintained; once the individual begins to use the machine, the PDA app records the details of the performance, including the weight level, the number of repetitions, the speed of the workout and the time elapsed. The PDA accesses a customized program to specify the order of an overall workout and walks the individual sequentially through the workout.

The advantage of the personalized apps is that an individual is able to fine-tune their workout to correspond to their preferences. The main aim is to allow a way not only to track a workout, but to improve the individual fitness regimen over time.

In one embodiment of the invention, the user specifies the parameters of the workout in the PDA app and the app program identifies the best program by comparing the preferred individual parameters to other programs and selecting the best choice from available options based on the individual preferences.

When the PDA app is used in a personalized way, it emulates a personal trainer, but automates the functions. Rather than merely manually tracking specific attributes of the exercise regimen, the PDA app customization allows the automation and adjustment of the workout as the workout unfolds in real time. In this sense, the advanced customized app is a form of expert system integrated into an automated exercise regimen.

The system also uses audio and voice recognition commands to activate PDA functions. In addition, the PDA uses audio to read out specific information.

The system uses multiple simultaneous functional processes. For example, a program is executed while data in the program are analyzed at the same time. In another example, an app program is executed while another app program is updated. Multiple simultaneous functions increase efficiency and facilitate multi-tasking.

(II) Exercise Machines

Exercise machines are a fundamental part of a modern workout. These machines include weight machines and aerobic (or cardio) machines. Weight machines generally are specialized and focus on exercising a specific muscle group. Aerobic machine types include a stationary bicycle, an elliptical machine, a treadmill machine, Stairmaster machine and hybrids of these device types. The present system is able to accommodate new exercise machine types. Further, while single function machines are typical, the present invention is applied to multi-functional exercise machines. These multi-functional machines include weight machines that are targeted to multiple and diverse muscle groups.

This section is split into four parts, with reference to the main components of the exercise machines: (A) Machine sensors; (B) Machine computer; (C) Video interface; (D) Robotics component and; (E) Computer program.

(A) Machine Sensors

While some aerobic exercise machines include a sensor set to capture heart rate data and count calories expended, sensors are a critical component of the present system for all exercise machines. Sensors may be integrated into the machine by hardwire or by wireless. If wireless, they may be installed after the machine is originally sold and are thus backwards compatible. In general, sensors provide the eyes and ears of the present invention.

Sensors use wireless technology to transmit data to the machine computer and to each individual's PDA. In one embodiment, sensors transmit data to actuators in the machine in order to activate a specific function.

Sensors record data, pass the data to a computer (in the machine or a PDA) and activate a program threshold to perform a function.

The sensor data for weight machines include machine condition and an activity journal. This data also include the specific weight selected, the number of repetitions used and the identification of the user.

The sensor data for aerobic machines include user heart rate counter, calorie counter, machine activity journal and relative user position. Sensor data in aerobic machines are used by a customized app to dynamically organize and optimize each individual's workout.

In one example of the use of the sensor system, once the machine sensors are activated by touch by a user, the machine downloads the app program with exercise program data details directly to the machine from the PDA. An electronic handshake process is activated after the sensors are activated.

In addition to the sensors in each exercise machine, in one embodiment, the motion sensor is wearable in order to use for tracking a user's aerobic activity. In these cases, the sensor interacts with the PDA app to record and track exercise data about the user's performance.

(B) Exercise Machine Computer

Each exercise machine is controlled by a computer. The computer generally consists of a chipset with a microprocessor controller, memory chips to store a computer program and a database for storing and retrieving information. The computer may consist of a system-on-a-chip that integrates the chipset circuit architecture.

Each machine's computer controls the main exercise functions. In the case of a weight machine, the computer controls the specific weight used. The computer counts the repetitions used. The computer also accesses the computer sensors to identify information about the user.

The machine computer accesses the PDA app to download a specific program that is used to customize an individual's workout. Once downloaded, the computer program modifies the exercise machine's program configuration. The exercise machine activates a specific function according to the specific program.

When an individual touches a sensor, the individual's PDA app is activated and information is collected by the exercise machine to update its program parameters. The individual's information stored in the PDA app, including the program parameters, are retrieved wirelessly by the machine computer and stored in memory.

When more than one individual activates a machine sensor, the machine prioritizes the activity between the individuals and selects a sequence that gives one individual access at a time.

(C) Video Control Screen

Each exercise machine in the present system uses a video screen for user activation and access. The video user interface of the exercise machines may be touch screen to enable specific graphic usability. One of the advantages of using a video screen is the ability to download video images upon request.

The video control screen in each machine interfaces with the machine computer to provide information to the user. The user is able to access the video control screen in an intuitive process.

The video control screen is used by the user to modify machine settings in real time. Specific controls (arrows that modify functions) are used to move the user through a program in order to control functions in a specific exercise.

When a PDA app downloads to an exercise machine, a customized program is activated that is observable in the video control screen. The user is able to modify the program by changing settings in the control screen of each machine as well as in the PDA screen.

In an additional embodiment of the system, a screen is used in a laptop computer to interface with the user. In still another embodiment of the system, a video screen is employed in a stand-alone kiosk (or computer) on the gymnasium floor. Users access the kiosk for interactive information. Users can transfer information from the PDA to any video screen for ease of use.

(D) Robotics Component

In the case of weight machines, in order to provide automation control functionality, the machines contain a robotics component. In this case, a "spine" mechanism is used behind the weight apparatus to adjust the pin to different amounts of weight.

When a user customized program is downloaded to a weight machine, the machine computer activates the robotics component to mechanically adjust the position of the pin along the spine to a new setting according to the preferences in the program.

The user in effect touches the machine's sensor array and activates the customized program, which accesses the machine's computer. The machine's computer then activates the robotics component to shift the pin's position in the weight mechanism to a specified weight level. The machine automatically adjusts the weight level. The new weight level is listed on the video interface of the machine and on the PDA.

Once the individual uses the machine at the new and preferred weight setting, the robotics component of the machine will either remain at the current setting or will return to a default setting.

An individual may change the setting manually by indicating a new weight setting on the video display of the machine or on the PDA. The exercise machine then automatically adjusts the weight setting to the new preferred weight by activating the robotics component and readjusting the position of the pin to a new weight setting. The new weight setting is then recorded in the exercise machine computer memory and in the PDA memory.

The pin adjustment mechanism of the robotics component of the exercise machines allows fitness machine automation processes that are integrated into a computer network.

(E) Computer Program

While each exercise machine has a computer program in the computer controller, the present system allows adaptation of the machine computer program by addition of a PDA app program.

In order to implement the PDA app into an exercise machine computer program, the PDA app sends out an applet to the exercise machine. The applet is received by the exercise machine computer program and activates a specific function in the computer program. In effect, each applet is a specialized program that activates a specific function in the exercise machine.

The exercise machine requests specific information about the applet by directing an inquiry to the PDA app. The PDA app sends out a handshake to the exercise machine computer controller. In some instances, this handshake may be initiated by a user tapping a machine sensor.

Information about the specific performance of the individual on each exercise machine is then recorded on each exercise machine as well as on the individual's PDA app.

The specific app, including customized apps, are used to program the machine to the user's specifications. The data that are recorded are then tracked and analyzed by the PDA app and then uploaded to the Web site database for modeling and personal exercise program modification and optimization. The individual's exercise program is then modified and updated.

When new app features or new apps are available on a Web site, they are downloaded to a PDA and activated when interacting with a specific exercise machine.

Some of these processes and techniques may be used beyond the specific exercise machines alone. In some cases, the machine computers and video interfaces and PDAs are networked to display video information on exercises involving free weights, yoga poses and stretching as well as specific sport activities. If an individual has access to specific aerobic exercises, this system will allow the disaggregation of aerobics group classes and allow the personalization of aerobics exercise.

(III) Free-Motion Sensor System

In one embodiment of the system, sensors are installed in bands that are used by users to track specific motions during exercises. In one implementation of the sensors, the bands are placed at points along the user's main joints (wrists, elbows, shoulders, hips, knees and feet) and points on the torso. In another implementation, the sensors are integrated into pants and shirt.

The system contains a tracking component in the PDA to track spatial motion of the sensor pattern. A three dimensional matrix map is built to organize the pattern sequence as the user performs an exercise or motion. The sensor motion is tracked within the 3D matrix. In another embodiment, a computer is used to track the user pattern sequence created by their exercise motions.

As the user performs a sequence of exercises, the information from the sensor array is recorded by the PDA app.

The sensor sequence pattern is then analyzed by the PDA and by the cloud-based database modeling system. The system model accesses a database of specific exercises. The sensor sequence pattern performed by the user is then compared to the database of accurate and optimal motions for each exercise. The model outlines ways for the user to improve the exercise.

The cloud-based database downloads the model information to a PDA or to a remote computer with a video interface. The computer displays the individual user exercise as recorded by the sensor data pattern. The computer display is used to compare the correct exercise motion to the actual user motion. The user then makes corrections to the exercise. This process repeats until the user's exercise experience is improved and mastered.

(IV) Database Management Systems

Databases perform a critical function in the present invention. The databases of the exercise machine, the PDA app and the Web site are networked. In effect, each of these platforms is integrated in the present system by using the database management system that consists of computer controllers, software programs and functional equipment. The database management systems are divided into four main categories: (A) Cloud-based components; (B) Data; (C) Software as a Service (SaaS) and; (D) Remote access.

(A) Cloud-Based Components

The Web has evolved to include a complex network of computers. In the context of cloud-based computing, integrated circuits are added and subtracted over time in computer "farms" in different locations. Data in cloud-based computers are stored in distributed databases. As specific computers in the cloud (i.e., computer network) are added and subtracted, the database management system is constantly updated so as to accommodate data storage and retrieval in different locations.

When a computer program that applies to the present system is written, it is uploaded to a database in a set of computers for storage. The computer program is then accessed by a computer and retrieved from the cloud-based computer network. The computer program is also accessible by a PDA or remote computer. The PDA or computer then downloads the computer program from the network computing database system.

This process allows software programs to be constantly modified. The modified computer programs are able to constantly update the computer and PDA software programs over time. This capability provides the advantage of adding software program features and automatically updating programs. For instance, a PDA software program app may receive an update of a specific feature that will then be activated in an exercise machine. As new features and apps are developed, they are accessible from the cloud-based database system. In one embodiment of this system, an individual will register with a service plan that consists of pushing regular updates of high grade apps over time. The apps and app features may be regularly downloaded to the PDA app automatically.

Software is automatically downloaded from the cloud-based computer network directly to the exercise machine as well. This process constantly updates the exercise machine software programs with new features.

Access to the cloud-based computer network allows the PDA to automatically back-up data directly to the cloud as well as receive software programs from the cloud.

In effect, the cloud-based computer network and database management system acts as a "locker" for the user to store and access individual programs, store workout data, track workout data and analyze the data. This system has numerous advantages in the organization of data as well as the active functional application of the data in the process of a customized workout.

(B) Data

Data are used in the present system to store information about a user's workout in the cloud-based computer network databases. The data are accessed by the PDA, the computer or the exercise machine each time a computer program activates an exercise machine. In addition, data are uploaded from the PDA, the exercise machine and a computer to the cloud-based database system.

Data may be used in a variety of categories in the present system. Data consist of active recording and storage of workout information. But data may consist of videos of specific types of exercises and information on health supplements, diet and health-related promotions. Ultimately, the data available to the system are encyclopedic.

The data are formatted to be used by multiple platforms, including the cloud-based database system, the computer database system, the PDA database system and various exercise machine database systems.

(C) Software as a Service (SaaS)

Increasingly, software is seen as a utility. Rather than buy a software program and have limited use of the static program, software programs are sold for a continuing fee. The advantage of using software on an ongoing basis is that the programming is continually upgraded. At each new use, the latest software program version is available, thereby benefitting the user. The use of cloud-based computing allows a seamless access to SaaS. The use of SaaS converts software to a Web-based utility that is always accessible, constantly upgradeable and interactive with storage and analysis facilities.

The present invention uses the SaaS system model to apply to the physical fitness system. One of the advantages of implementing a SaaS system is the interactive component that applies to the dynamic fitness environment.

The present system uses several services that are provided by a SaaS system. First, the present system allows customization of an updatable exercise program for each individual. Second, the system provides automated tracking of workouts. Third, the system provides analytics of both individual and group workouts. This allows the system to provide performance evaluations and to supply recommendations of exercise program changes. Fourth, the system allows the user to modify the programming to suit their preferences in real time. Fifth, the system allows the software to interact dynamically with exercise equipment or with sensor arrays.

Further, when software is updated, new features and additional applications are available, they are automatically provided on-demand to customers.

One advantage of SaaS system applications to the exercise fitness system is that a range of services are available for a differentiated fee. When a customer wishes to add a software feature, application or service to their personalized program, they may simply pay a fee. The Web-based system instantly performs the request. The SaaS system is modular, thereby allowing a smorgasbord of differentiated functions available to customers at any time.

(D) Remote Access to System

One of the advantages of the automation and Web-based aspects of the present system is that select third parties may remotely access the customer information and make assessments and modifications to the personalized exercise program. In the most obvious case, a physician may monitor the user's program, make an independent analysis and make modifications. Once the exercise program is modified, the individual user will make corresponding changes in the program schedule. The ability to have a physician actively and remotely modify an exercise schedule allows the identification of irregularities and pathologies. For instance, heart rate monitoring during exercise may be a critical indicator of health problems. If a problem is determined, aerobic activity may have to be limited.

The remote access feature makes possible an independent evaluation by a personal trainer to supply customized recommendations and program modifications.

Finally, the remote access capabilities of the present system allow physical therapists to address a patient's injury in real time. This interactive ability with a third party allows an exercise regimen to be tailored to an injury for rapid healing. The process is integrated with a regular workout session and thus extremely efficient and money saving. The third-party merely accesses the individual user exercise program and makes modifications necessary to accommodate an injury. Particularly for individuals in remote areas, this system is a solution to a complex treatment problem. The remote system that includes program modification accommodation for injuries allows a faster recovery time.

The system analyzes the individual's workouts regularly and detects anomalies and irregularities. The system then initiates a contact with a third party, such as a physician, to review the data and request a meeting with the user or a modification of the exercise program.

The third parties access a customer's account on a Web site and receive data on the exercise and diet program. The third party requests authority to make a modification to the program and suggests reasons for the modification. The software system then records the changes and lists the proposed modifications alongside the original exercise and diet program. Upon reviewing the suggestions and the alternative program, the user then selects whether to update the program to include the modifications. Once selected, the modified exercise and diet program is then added to the user schedule. After an injury is healed, the user activates the original exercise and diet program and returns to the original program and schedule.

(V) Modeling

The present invention uses analytical processes to calculate, organize, analyze and model individual exercise data and group exercise data. The modeling component is divided into: (A) Analysis and Model Building; (B) Analysis and Feedback and; (C) Personalized Promotions.

(A) Analysis and Model Building

The data are collected by the exercise machines and the PDAs and uploaded to Web based network storage. The data are then analyzed. Information about a user's workout is tracked and modeled. Multiple exercise sessions of each individual are analyzed as well to identify patterns.

The information analyzed includes heart rate, calories expended, weight amounts, number of weight repetitions and relative exercise positions. The information on each exercise in an individual's exercise program is input into data storage and accessed to construct models.

A model is built to plot each individual's workout relative to other workouts. The model organizes the individual by gender, age, general profile and relative performance.

Overall, a model is built based on the collection of information about a group of individual's workouts over time. This aggregate data set is useful in order to compare individual exercise programs. The pattern of an individual's behavior is analyzed by comparing it to the pattern of group behavior. Individual workouts can be compared to an own individual's record of workouts as well as to a group's record. From the comparison of these patterns, it is then possible for the model to rank each individual's performance within their own workout record and between other individuals.

Modeling of exercise performance is useful in order to develop probabilities of expected results for future exercise experiences, for both individuals and groups. These probabilities generally are useful to anticipate a range of exercise performance for specific individuals over time based on a set of criteria.

The use of modeling is valuable in order to identify areas for individual improvement. By identifying deficiencies in an individual workout, the system is able to make recommendations to improve an individual workout; these suggestions are then implemented into updated individual exercise programs.

The modeling system is able to display an individual workout alongside another workout. This comparison process may be made to (a) another workout for the same individual, (b) another workout for another individual or (c) an aggregate of a type of workout of a group of individuals. In addition, the analysis of group aggregate information is useful to display the relative performance of an individual.

Analysis of group exercise performance patterns is also useful in order to develop suggested improvements to an individual exercise program from data involving a similar group of individuals.

(B) Analysis and Feedback

Passive analysis and modeling is performed as described above. However, active analysis of exercise performance is also performed by the present system. In essence, updated data are used to modify and improve an individual's workout and to enhance their performance.

The automation components of the present system allow individual exercise performance data to be recorded, assessed, tracked and analyzed in real-time. This active analytical process allows the system to produce modeling results at the time that an individual is in the exercise process. The model then produces scenarios for a range of modifications for each individual to adapt their exercise program. The scenarios produce options that are selected by the individual in order to optimize the exercise program.

In one embodiment of the active feedback aspect of the modeling system, an individual performs a warm-up exercise, obtains an immediate analysis, generates model scenarios and selects a scenario option for a modified exercise program. The system automatically modifies the current exercise schedule to include the modified program based on the selected scenario. At another time, an individual will select another scenario option based on another model analysis of another workout and the system will update the exercise program accordingly. This process allows a modeling on-demand feature of the present system.

Since the system analyzes a group of individuals' workouts, the group modeling process recognizes patterns in the group that are sorted by multiple variables. The system then develops a macro-analysis based on the group modeling. This macro-analysis produces recommendations about specific exercise programs targeted to specific individuals based on identifying specific patterns in the larger group. This group analysis process, for instance, is able to identify trends among similar individuals' workouts.

The active feedback component of the modeling process allows a just-in-time aspect for each individual's workout. For example, an individual may stop their scheduled workout to request an analysis of a specific exercise, which they seek to modify and improve, before proceeding.

The active modeling feature allows the system to constantly track and analyze an individual's performance. When an individual is performing below the expected range of an exercise performance, the system will seek to modify the exercise schedule to accommodate the individual to allow them to achieve their goals.

In one embodiment of this process, when an individual seeks an aggressive workout beyond their ordinary exercise program, the modeling component of the system automatically modifies the individual workout on-demand to accommodate the requested option.

In another embodiment of the process, an individual may change the workout based on model scenario information at any juncture in the exercise program. In effect, based on the latest model information, they are able to select a new option to integrate into their exercise program, which then automatically updates their exercise schedule.

The modeling component of the present system uses a set of variables related to the individual workout to perform an analysis. These variables include: (a) amount of weight, (b) intensity level of aerobics, (c) order of sequence of exercise, (d), duration with each exercise, (e) number of exercises, (f) overall length of time of workout and (g) variety of exercises. Additional variables may be added.

The modeling variables are analyzed so as to solve multi-objective optimization problems. In one example relating to weight machine exercises, the model will recommend a weight level between too low and too high of a setting. In another example, the model will recommend a level between too few and too many repetitions. In the case of aerobic exercises, on the other hand, the model recommends between too little and too much intensity of exercise, between too slow and too fast of an aerobic speed and between too little and too long of length of an aerobic workout.

In another application of the active modeling and feedback component of the present invention, the system also applies to actively monitoring nutrition. In implementing a diet program with the present system, the system initially collects information about an individual profile and goals and then supplies a diet program based on preferences of modular options. The diet app is transferred to a PDA, which then actively tracks the diet options and schedule.

As the individual encounters a session with a set of diet options, the app records the selections and tracks the diet schedule progress. The diet program lists specific food options at specific times. The PDA app specifies options of what to eat at each meal time. The diet app requires an individual to specify what is actually eaten and when it is eaten. The diet app then records the data and the PDA uploads the data to a cloud-based database system.

The individual's diet program is tracked and analyzed by the modeling system. The individual diet data is modeled. The model analyzes the diet program and compares the actual individual results. The model recommends adjustments to the diet program and recalibrates the schedule. Recommendations, as well as individual requests, are input into the diet program. The diet program is dynamic since it allows feedback from the model to update and modify the program and the schedule until the individual achieves their goals.

(C) Personalized Promotions

Increasingly, in electronic systems, promotions are customized and automated. The ability to provide customized promotions is based on access to, and analysis of, individual data sets. Since the present invention involves collecting and analyzing data sets to track individual exercise performance, the system is also able to supply customized promotions directly to an individual precisely when the promotion is targeted the most efficiently. Before a workout, health supplement coupons may be offered. After a workout, protein drink or sports drink coupons are offered. Specific clothing, shoes and sports equipment (rackets, balls, etc.) are also offered to specific individuals that are most likely to be receptive to these offerings. In addition, education about specific exercises, exercise equipment and sports are provided as well as information about general health, injuries and nutrition. Further, the promotions include targeted references to the present system's own advanced features.

The promotions are provided by sponsors of the present system. Advertisers will have access to generic or private information obtained in the process or recording, tracking and analyzing individual and group exercise performance data. The aggregate data on groups of individuals are used by advertisers and sponsors to target their products to specific individuals at key times.

DETAILED DESCRIPTION OF THE EMBODIMENTS

The present invention is designed to provide a customized automated exercise program to individuals to obtain an optimized fitness experience.

There are three main embodiments of the present invention. The first involves creation and implementation of an exercise regimen for each individual. The second involves development and implementation of a customized exercise regimen, including with modeling and feedback mechanisms. The third involves using the system technologies and techniques to facilitate a completely automated customized exercise regimen for each individual with modeling and feedback mechanisms.

First Embodiment

In the first embodiment of the invention, an individual registers data with the system and designs an exercise regimen. In this embodiment, which emulates an expert system, once the individual registers with the system, the system compares the individual's profile with a set of similar profiles in a matrix and produces a recommended exercise regimen for the individual.

In general, after an individual completes an initial fitness assessment, the data are uploaded to the network database and analyzed. The system compares each individual's circumstances with similar individual fitness programs and delineates an initial exercise program along with a schedule of exercises. After an initial individual experience with the exercise program, the system tracks the exercise information and uses the feedback of the actual experience to update and refine the exercise program. This process repeats.

In this embodiment, individual users have access to a set of exercise videos that are organized by exercise type. The videos are downloaded on demand at different phases of the workout as explanatory advice for specific exercises.

In addition, personal trainers are available on-demand to answer questions about specific exercises and design of an overall exercise program.

Since different personal trainers have different styles of training, the trainers are organized into groups according to specific categories. When an individual seeks an expert in a specific category, they are forwarded to a set of trainers and are supplied with a choice of trainers, along with specific information (including ratings by past users) about the trainers.

In this embodiment of the invention, each individual rates their workouts and this exercise information is loaded into system.

The system organizes an exercise "diary" that includes an activity tracker. As each individual completes an exercise, they enter information about the exercise into a PDA app. This information is then uploaded to the Web storage facility for storage. This data is then analyzed to supply information to the user.

In this embodiment, the exercise program may be modified at different phases. Each individual is provided with a set of scenarios, or options, in order to modify the workout at different phases. For instance, at one time, the aerobic activity may come first, while the weight training may come later. In another instance, the order of the weight training will change in order to train different muscle groups on different days. The individual user is able to control the options and scenarios in this embodiment.

In one implementation of this embodiment, at each stage of a workout, a user is provided with multiple options in the PDA, in which the individual is asked what they would like to do at each stage of the exercise process.

Second Embodiment

In the second embodiment of the present invention, an individual is integrated into a customized fitness program. Once the individual completes an initial assessment about their profile, goals and performance record, the system compares the individual to major categories of the fitness program by accessing a matrix of categories of individual fitness programs. The system generates a customized exercise program consisting of a weight training component and an aerobic component. The program also consists of a diet program.

Because the system uses software-as-a-service components, the exercise program is constantly updated based on the latest information obtained about each individual's workout. As the individual performs specific weight and aerobic exercises, information about these experiences is constantly updated, tracked and uploaded in the Web network storage.

Once data are stored about actual workouts, the modeling system analyzes the workouts and provides recommendations based on individual goals and pattern analysis of sets of individual and group workouts. The modeling data is used to generate a set of scenarios that are forwarded to each individual in real time. As the individual completes an exercise, the data is uploaded to the Web network and the PDA or exercise machine video display records downloaded modeling data and recommendations for improvements. The exercise schedule is updated based on these recommendations.

The modeling data are also used to present targeted promotions to individuals at different points in the exercise program.

In one implementation of the second embodiment, the system is presented with a goal to keep the user's heart rate at a specified level for a specified period of time. The system sends a wireless signal from the Web site to the exercise equipment to maintain a specific heart rate level. The system uses feedback from the exercise machine and fuzzy logic-based algorithms to continuously calculate the rate of change of activity in the machine in order to calibrate the heart rate to meet the goal. The equipment changes settings in order to keep the heart rate stable until the goal is met.

As in this example, the fitness program is monitored and tracked in real time and supplies feedback. Individuals may selectively modify their workout regimens by making changes to the exercise program and to the schedule.

The system models a set of options for each weight and aerobic exercise activity. The system, for example, identifies a set of scenarios for each exercise and allows the user to select a specific scenario trajectory. This approach is useful in order to set improvement goals over time.

Third Embodiment

In the third embodiment of the present system, the system produces a fully automated exercise regimen. After the individual profile is assessed and an exercise program is generated, the program is forwarded to the individual's PDA app. The PDA app sends the data on the selected weight level and number of reps to the various automated weight machines. In another implementation, the system downloads the program directly to each weight machine. When the individual activates each machine, the weight levels and programmed number of repetitions are registered for that individual's exercise. The individual then completes the weight exercise for that machine. The machine sensors record the specific information of the individual performance and upload the data wirelessly to the PDA. The PDA periodically uploads the data to the Web network storage. This process is repeated for various weight machines in the exercise program.

In the case of using an aerobic (i.e., cardio) machine, the system downloads the specifications of the individual's aerobic exercise program into the user's PDA. In another implementation, the system downloads the program directly to the exercise machine. A customized aerobic exercise program is activated once the individual activates the exercise machine. The user then performs the exercise while accessing the sensors to update workout information. The updated information is then uploaded from the exercise machine to the PDA and to the Web network storage facility.

Information on the individual's workout is analyzed by the modeling system. The modeling system analyzes the user's workout experience and supplies recommendations in real time. As the individual is in the process of a specific set of exercises, they may request advice on a specific exercise from the system. The system supplies a set of choices based on a set of scenarios. The individual then selects a specific scenario and proceeds with this exercise approach.

The system also uses the modeling information to supply promotions to users in real time. As a user is performing a specific exercise, the system will provide coupons from advertisers relating to the exercise. Before a workout, the system will recommend specific clothes, shoes, equipment and supplies. After a workout, the system will recommend diet and health supplement information.

At each stage, the system updates and refines the exercise program to develop a customized and automated fitness experience that is optimized for each individual.

Reference to the remaining portions of the specification, including the drawings and claims, will realize other features and advantages of the present invention. Further features and advantages of the present invention, as well as the structure and operation of various embodiments of the present invention, are described in detail below with respect to accompanying drawings.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes in their entirety.

DETAILED DESCRIPTION OF THE DRAWINGS

FIG. 17 is a set of schematic drawings showing the process of automatically moving a pin on an exercise machine.

FIG. 29 is a flow chart showing the process of using a diet program that actively tracks an individual's diet with a PDA.

FIG. 30 is a flow chart showing the process of interaction with an exercise machine to refine a user's workout.

DETAILED DESCRIPTION OF THE DRAWINGS

The computer automated physical fitness system is comprised of a set of component elements. These elements consist of exercise machines that are networked with portable computers and personal digital assistants (PDAs) that include smart phones and tablet computers. The digital devices send and receive software program code and interact with the exercise machines. Software programs and apps are downloaded from the Internet on-demand and are customized for each user.

Figure 1:
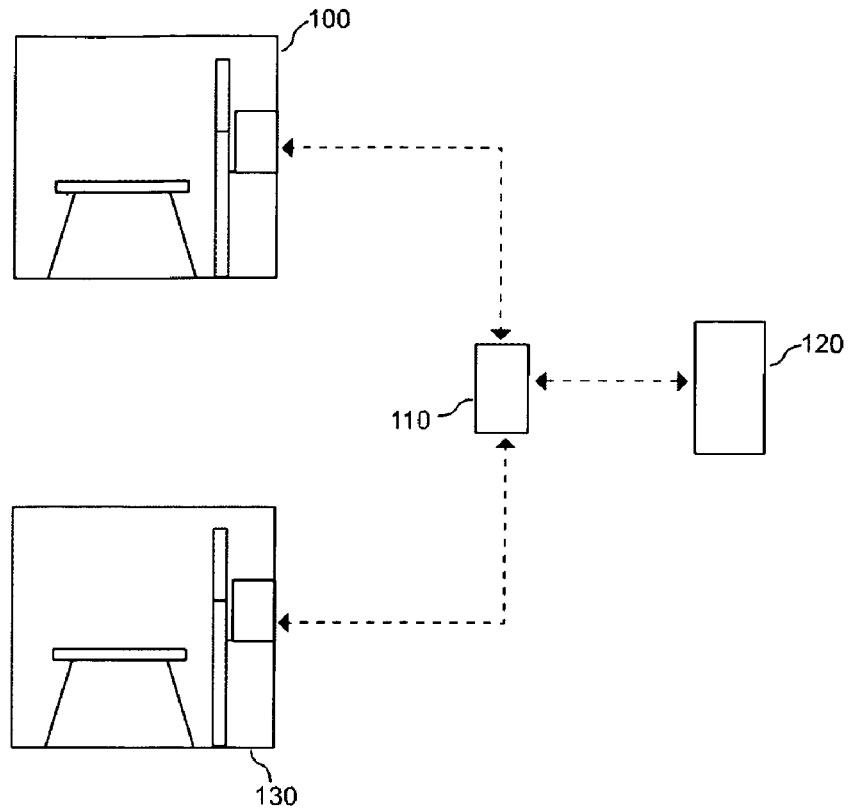
FIG. 1 is a schematic drawing of two exercise machines interacting with a personal digital assistant and the Internet.
Figure 2:
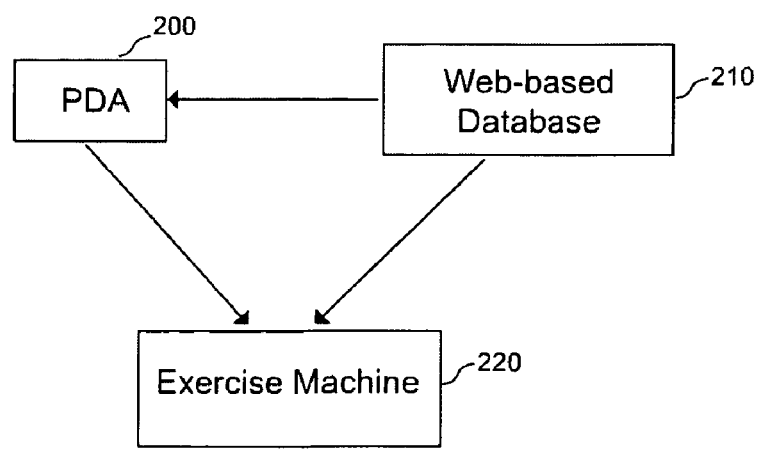
FIG. 2 is a schematic drawing showing the connections between an exercise machine and a personal digital assistant and a Web-based database.
Figure 3:
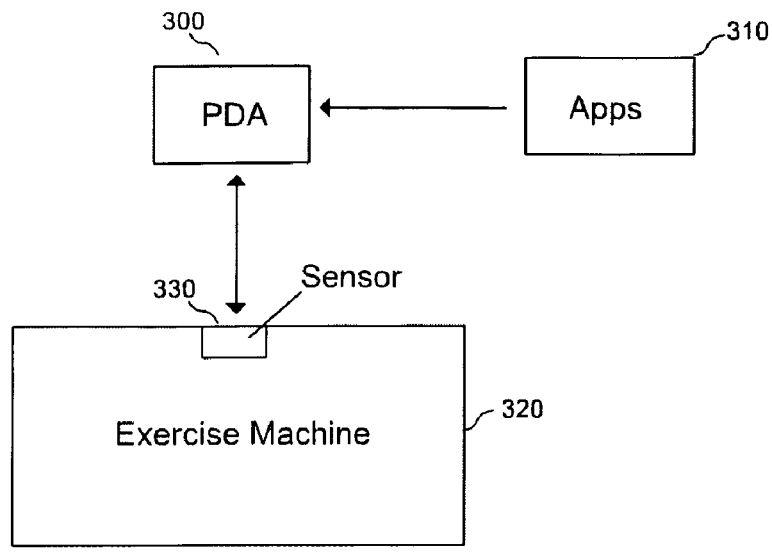
FIG. 3 is a schematic drawing showing an exercise machine with a sensor and a PDA that interacts with the exercise machine and that receives apps from the Internet.

FIG. 1 shows two exercise machines (100 and 130) that interact with a PDA (110), which interacts with a Web site (120) to send and receive software programs. FIG. 2 shows the PDA (200) downloading software to an exercise machine (220). A Web-based database (210) downloads software to the PDA (200) and directly to the exercise machine (220). FIG. 3 shows an exercise machine (320) containing a sensor (330). The PDA (300) downloads the software to the machine (320) but also receives sensor data from the sensor. Software apps (310) are downloaded to the PDA.

Figure 4:
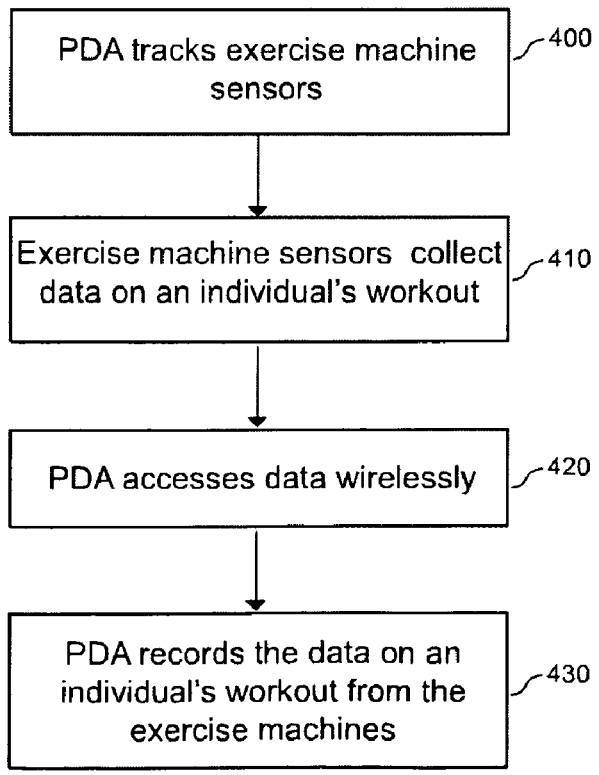
FIG. 4 is a flow chart showing the process of using the PDA to track an individual's workout.

FIG. 4 shows the process of using the PDA to track an individual's workout. After the PDA tracks an exercise machine's sensors (400), the machine sensors collect data on an individual's workout (410). The PDA accesses the data wirelessly (420) and records the data on an individual's workout from two or more exercise machines (430).

Figure 5:
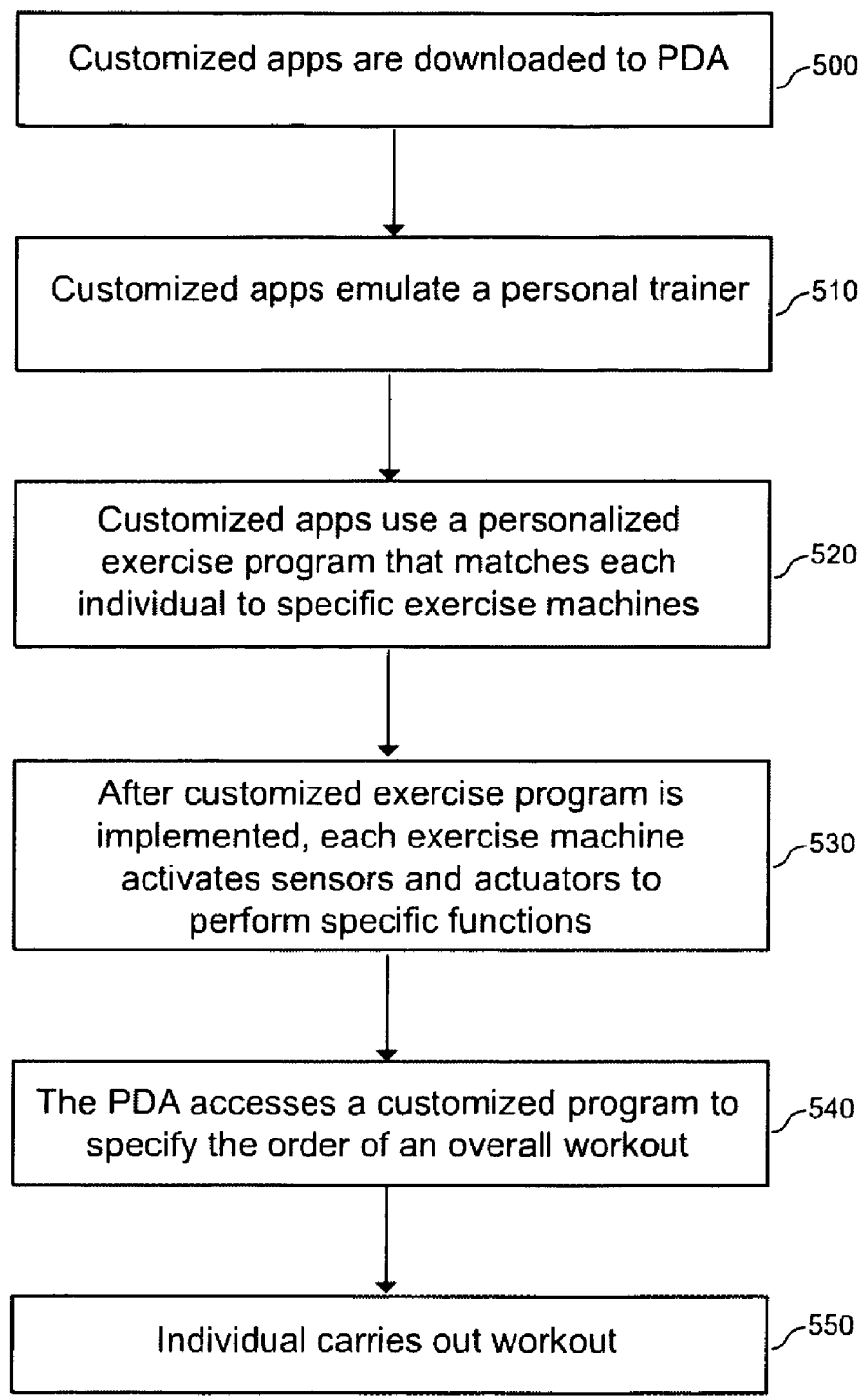
FIG. 5 is a flow chart showing the process of using customized apps in a personalized exercise program.

FIG. 5 shows the process of using customized apps in a personalized exercise program. Once the customized apps are downloaded to a PDA (500), they emulate the behaviors of a personal trainer (510). The customized apps then use a personalized exercise program that matches each individual to specific exercise machines (520). After a customized exercise program is implemented, each exercise machine activates sensors and actuators to perform specific functions (530). The PDA then accesses a customized program to specify the order of an overall workout (540) and the individual carries out the workout (550).

Figure 6:
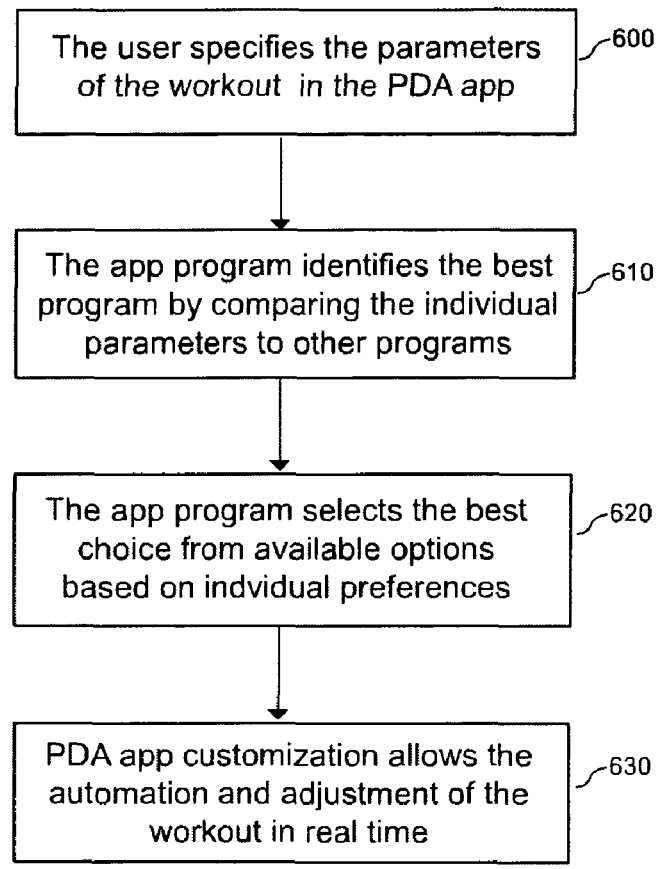
FIG. 6 is a flow chart showing the process of using the PDA app in the workout.

FIG. 6 shows the process of using the PDA app in the workout. After the user specifies the parameters of the workout in the PDA app (600), the app program identifies the best program by comparing the individual parameters to other programs (610). The app program selects the best choice from available options based on individual preferences (620) and the PDA app customization allows the automation and adjustment of the workout in real time (630).

Figure 7:
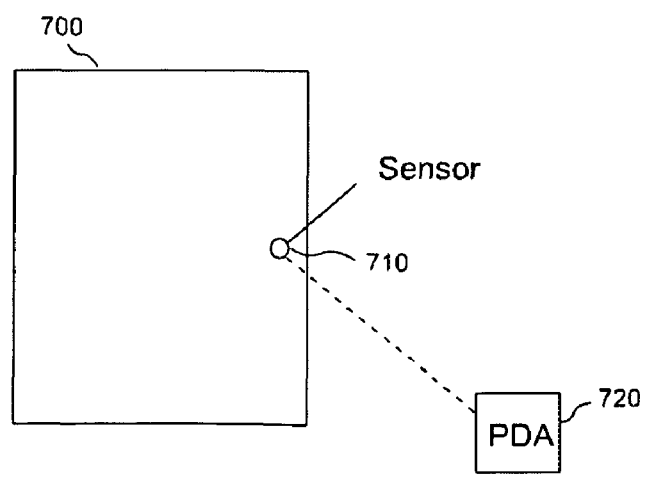
FIG. 7 is a schematic drawing showing an exercise machine with sensor sending and receiving a signal with a PDA.
Figure 8:
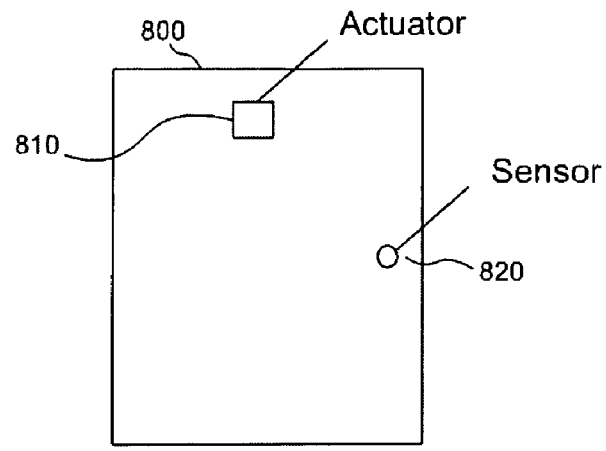
FIG. 8 is a schematic drawing showing the process of sending sensor data to an actuator to activate a machine function.
Figure 9:
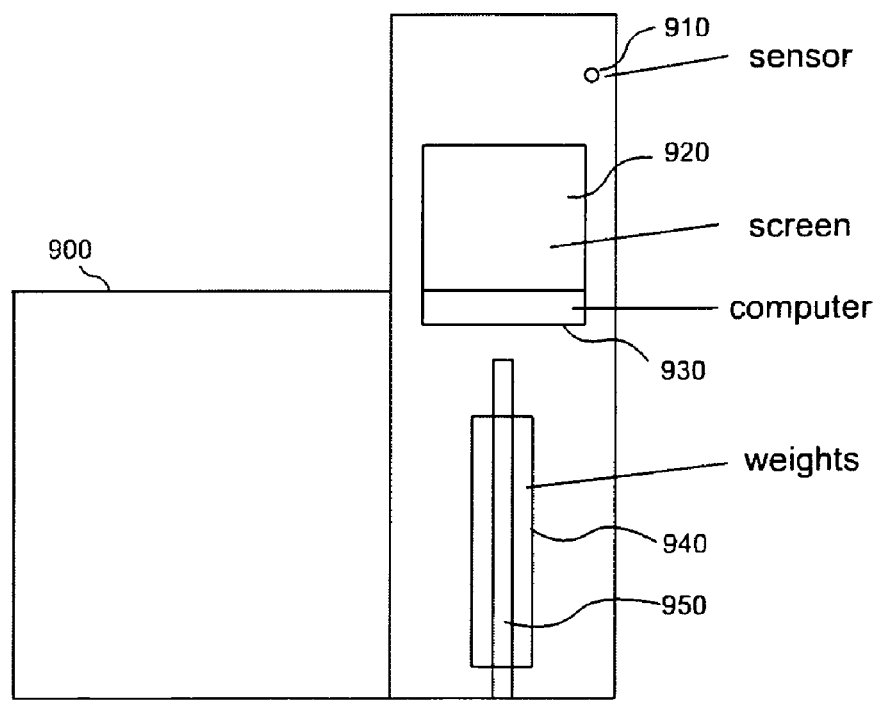
FIG. 9 is a schematic drawing showing a weight machine.

FIG. 7 shows an exercise machine (700) with a sensor (710) sending and receiving a signal with a PDA (720). FIG. 8 shows an exercise machine (800) with an actuator (810) and a sensor (820). FIG. 9 shows an exercise machine (900) with weights (940), a spine (950) for the weight movement, a computer (930), a computer screen (920) and a sensor (910).

Figure 10:
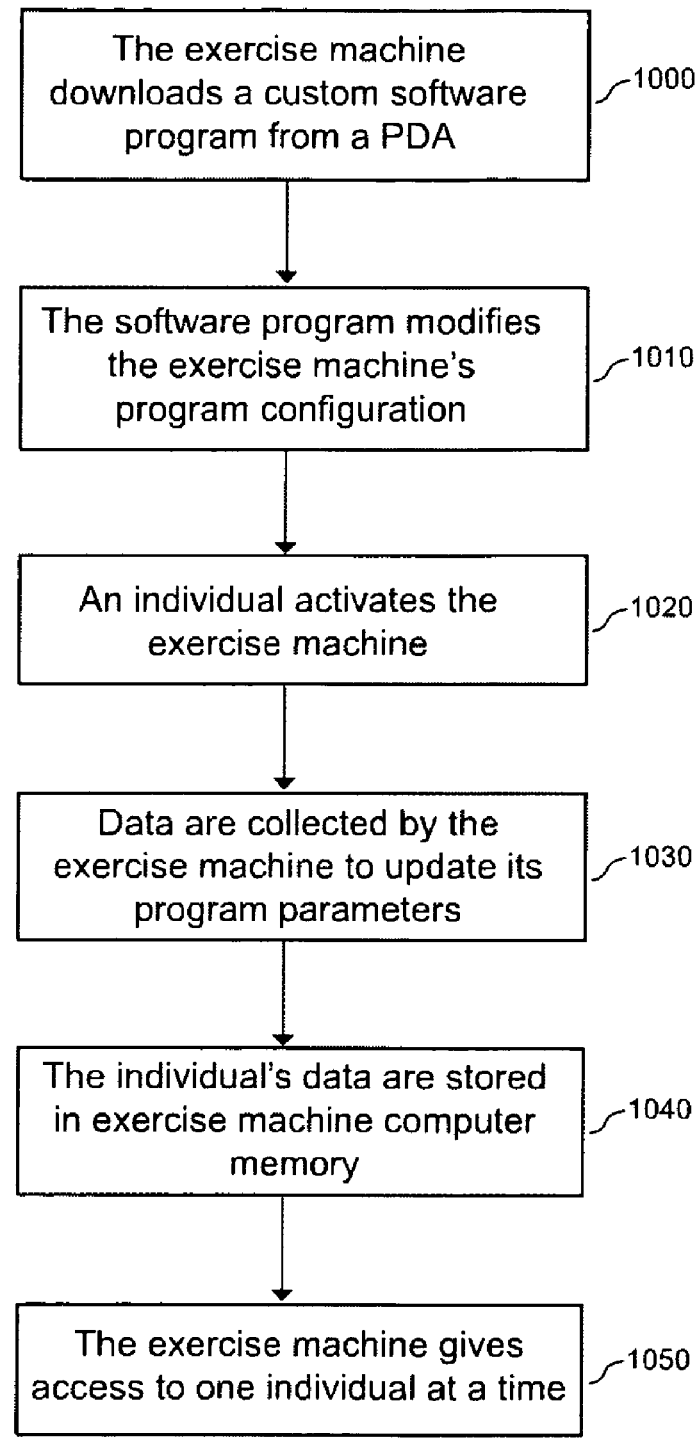
FIG. 10 is a flow chart showing the process of applying a software program to an exercise machine.

FIG. 10 shows the process of applying a software program to an exercise machine. Once the exercise machine downloads a custom software program from a PDA (1000), the software program modifies the exercise machine's program configuration (1010). An individual activates the exercise machine (1020) and data are then collected by the exercise machine to update its parameters (1030). The individual's data are stored in the exercise machine computer memory (1040) and the exercise machine gives access to one individual at a time (1050).

Figure 11:
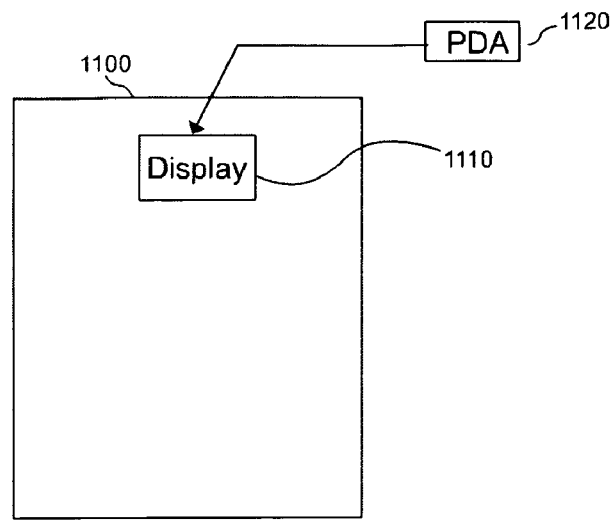
FIG. 11 is a schematic drawing showing a PDA downloading an app to a display on a machine.
Figure 12:
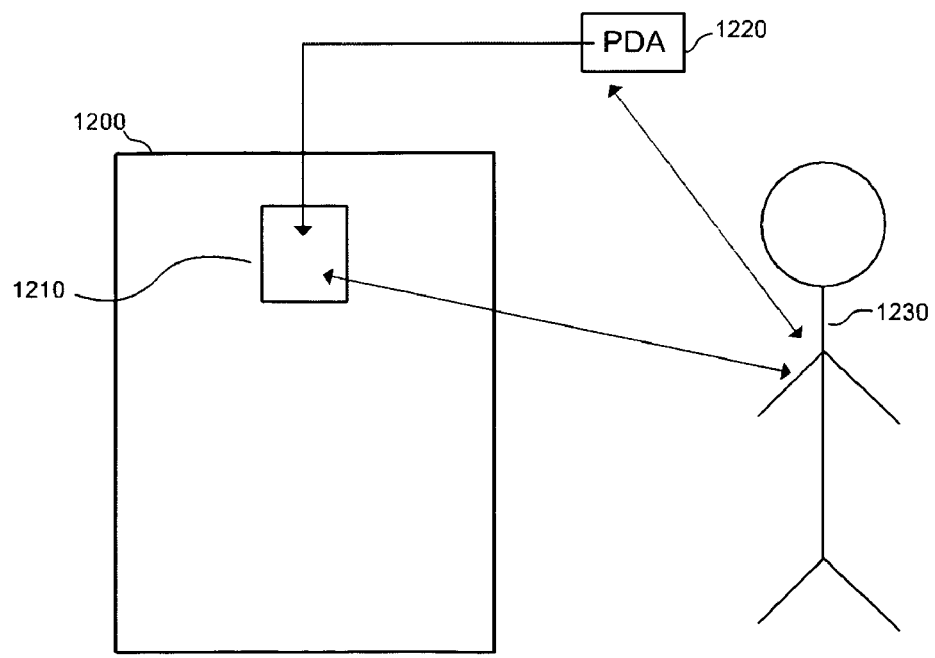
FIG. 12 is a schematic drawing showing the process of a user modifying a program at the PDA or control screen of a machine.
Figure 13:
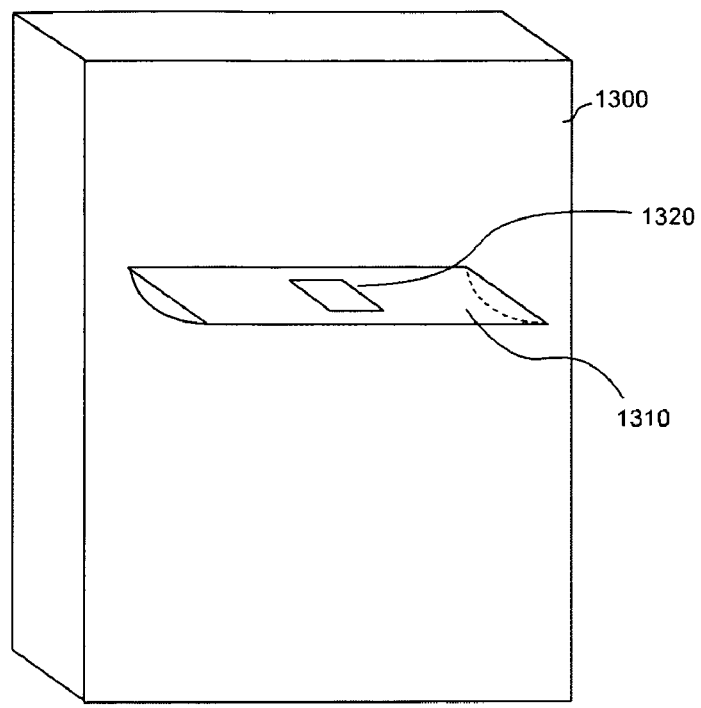
FIG. 13 is a schematic drawing of a kiosk with a computer used to control exercise machines.

FIG. 11 shows an exercise machine (1100) with a display (1110). The display receives software program code from a PDA (1120). FIG. 12 shows an exercise machine (1200) interacting with a user (1230). The user uses the PDA (1220) and the PDA interacts with the exercise machine display (1210) by sending and receiving signals. The user then accesses the display. FIG. 13 shows a kiosk (1300) with a console (1310) and a display (1320).

Figure 14:
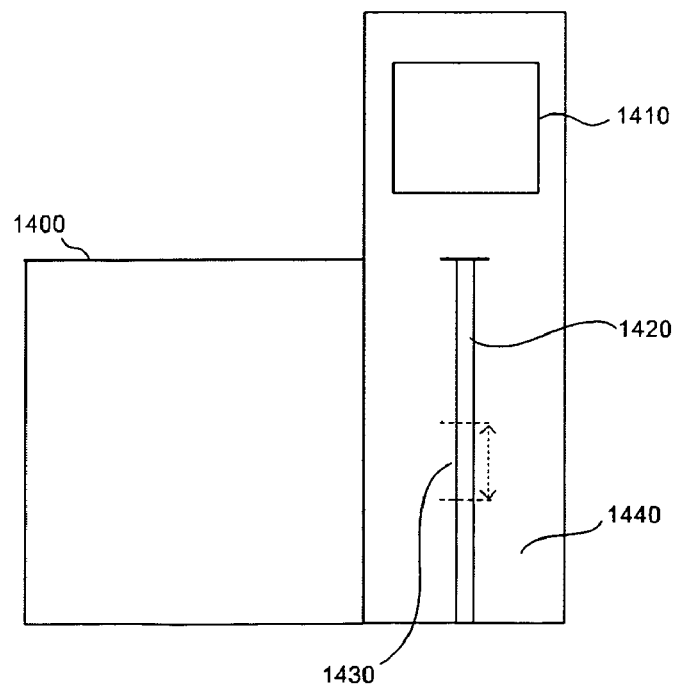
FIG. 14 is a schematic drawing showing a pin on an exercise machine spine as it moves automatically to conform to user specifications.

FIG. 14 shows an exercise machine (1400) with a spine (1420) for weights. A pin moves within a range of space (1430) on the spine. The machine has a display (1410) for a user to interface with the machine. The user may set the weight on the machine by accessing the display or may use the PDA app to automatically set the weight.

Figure 15:
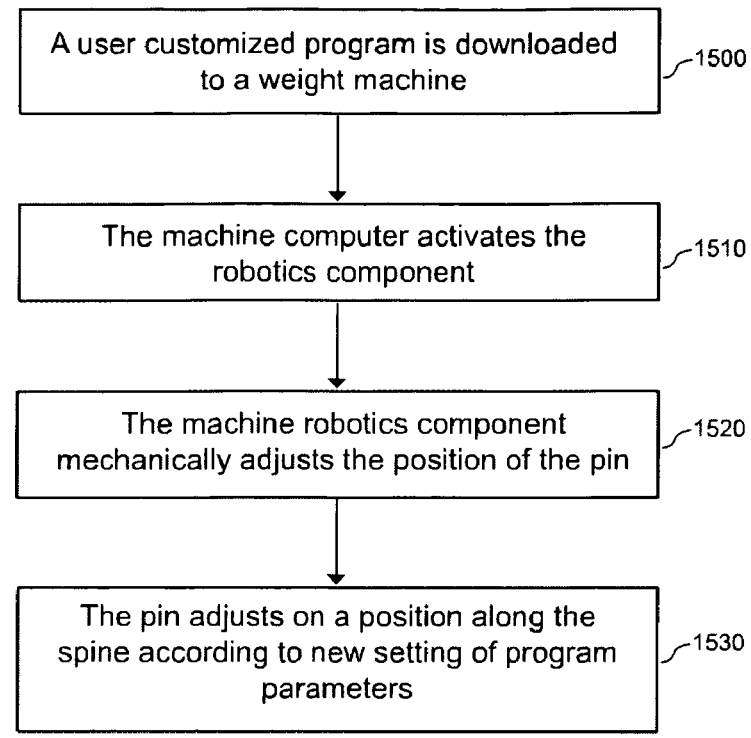
FIG. 15 is a flow chart showing the process of downloading a program to a weight machine and activating robotics components in the machine.

FIG. 15 shows the process of downloading a program to a weight machine and activating robotics components in the machine. After a user customized program is downloaded to a weight machine (1500), the machine computer activates the robotics component (1510). The machine robotics component mechanically adjusts the position of the pin (1520) and the pin then adjusts on a position along the spine according to the new setting of program parameters (1530).

Figure 16:
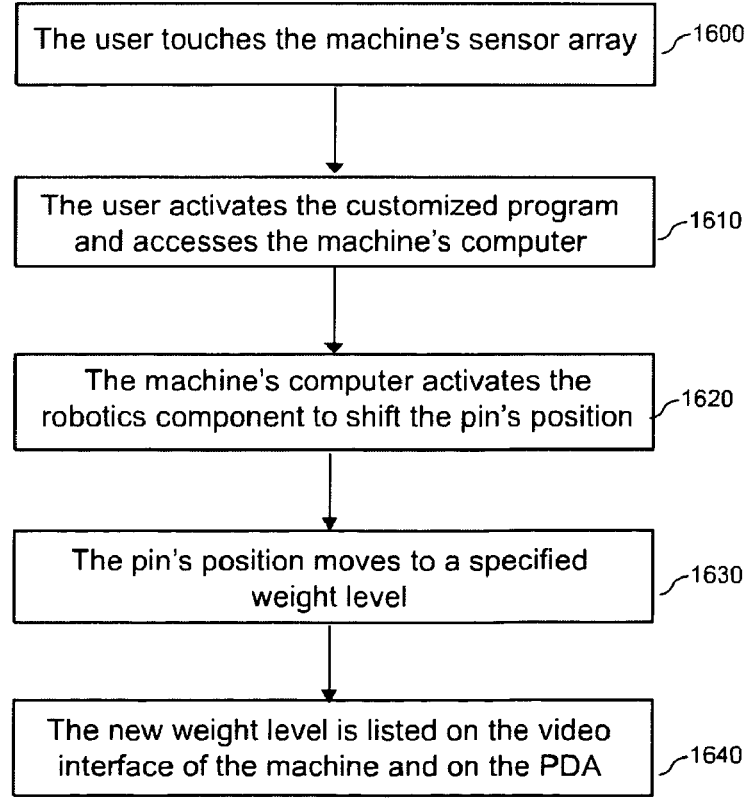
FIG. 16 is a flow chart showing the process of user interaction with a robotic exercise machine.

FIG. 16 shows the process of user interaction with a robotic exercise machine. Once the user touches the machine's sensor array (1600), the user activates the customized program and accesses the machine's computer (1610). The machine's computer activates the robotics component to shift the pin's position (1620) and the pin's position moves to a specified weight level (1630). The new weight level is listed on the video interface of the machine and on the PDA (1640).

FIG. 17 shows the process of automatically moving a pin on an exercise machine. In phase one, the pin (1720) is positioned at the bottom of the spine (1710) of the machine (1700). In phase two, the pin (1750) is positioned at the top of the weight stack on the spine (1740) of the machine (1730). Finally, in phase three, the pin (1780) is at the bottom of the spine (1770) of the machine (1760).

Figure 18:
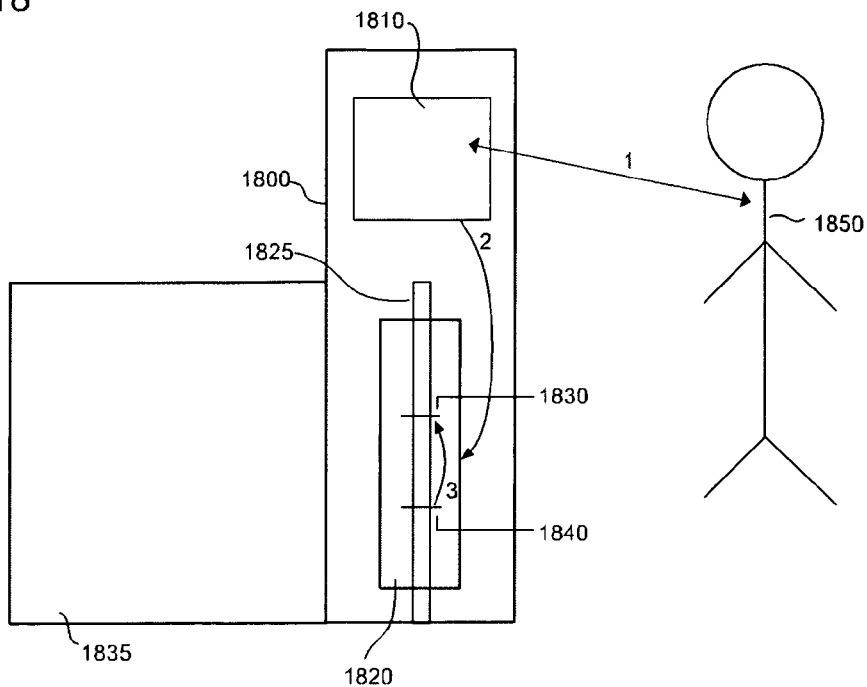
FIG. 18 is a schematic drawing showing the three phases of manually changing a program to change the pin position on an exercise machine.

FIG. 18 shows the three phases of manually changing a program to change the pin position on an exercise machine. In this drawing, the machine (1835) is shown with a display (1810) on the right panel (1800) of the device. The spine (1825) of the weight mechanism (1820) enables the movement of the pin from position 1830 to 1840. In this drawing, the user (1850) interacts with the display (1810) and selects a setting. This may also be done by selecting a setting in a user PDA and downloading the selected setting to the exercise machine. The display activates the computer to automatically move the pin from one position (1840) on the weight mechanism to another position (1830) to conform to the selected setting. Once the pin is moved, the weight selection changes and the user activates the weight machine by using a specific selected weight.

Figure 19:
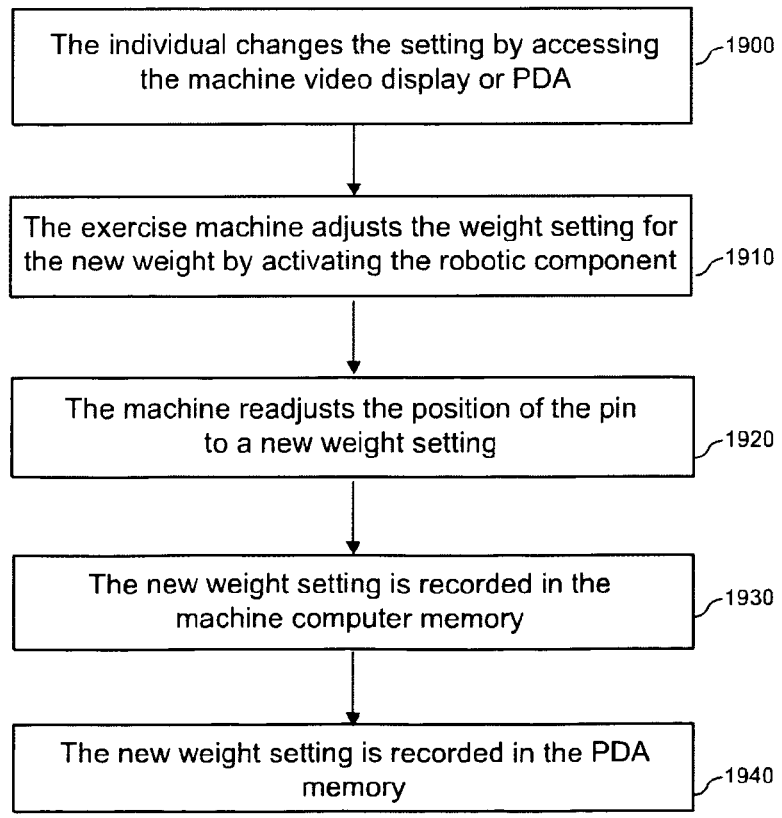
FIG. 19 is a flow chart showing the process of readjusting the weight setting in an automated exercise machine.

FIG. 19 shows the process of readjusting the weight setting in an automated exercise machine. After the individual user changes the setting by accessing the machine video display or PDA (1900), the exercise machine adjusts the weight setting for the new weight by activating the robotic component (1910). The machine then readjusts the position of the pin to a new weight setting (1920), the new weight setting is recorded in the machine computer memory (1930) and in the PDA memory (1940).

Figure 20:
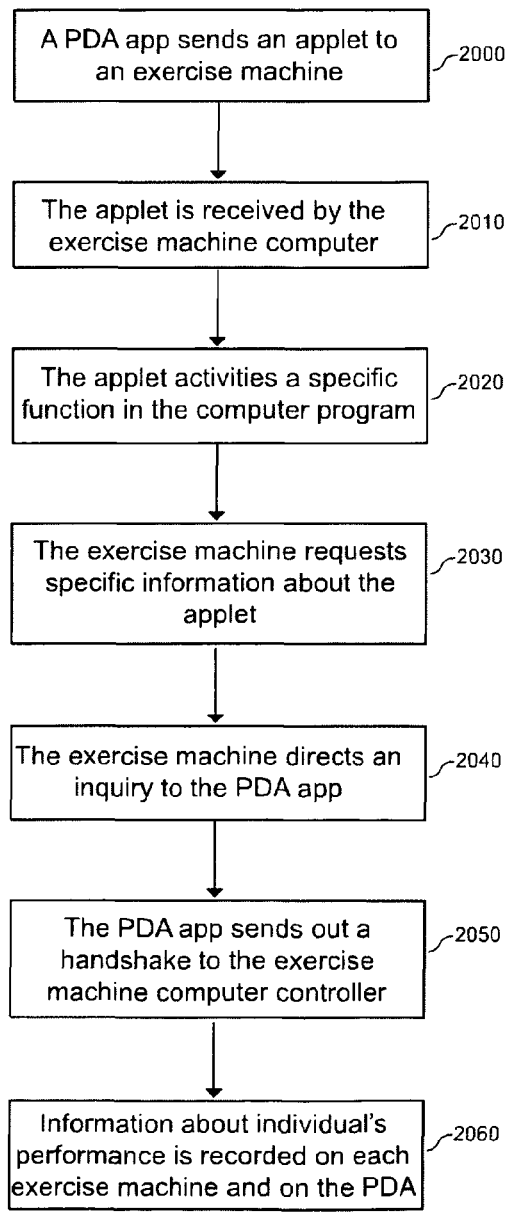
FIG. 20 is a flow chart showing the use of an applet to activate an exercise machine.

FIG. 20 shows the use of an app let to activate an exercise machine. After the PDA app sends an applet to an exercise machine (2000), the applet is received by the exercise machine computer (2010). The applet then activates a specific function in the computer program (2020) and the exercise machine requests specific information about the applet (2030). The exercise machine directs an inquiry to the PDA app (2040) and the PDA app sends out a handshake to the exercise machine computer controller (2050). Information about the individual's performance is recorded on each exercise machine and on the PDA (2060).

Figure 21:
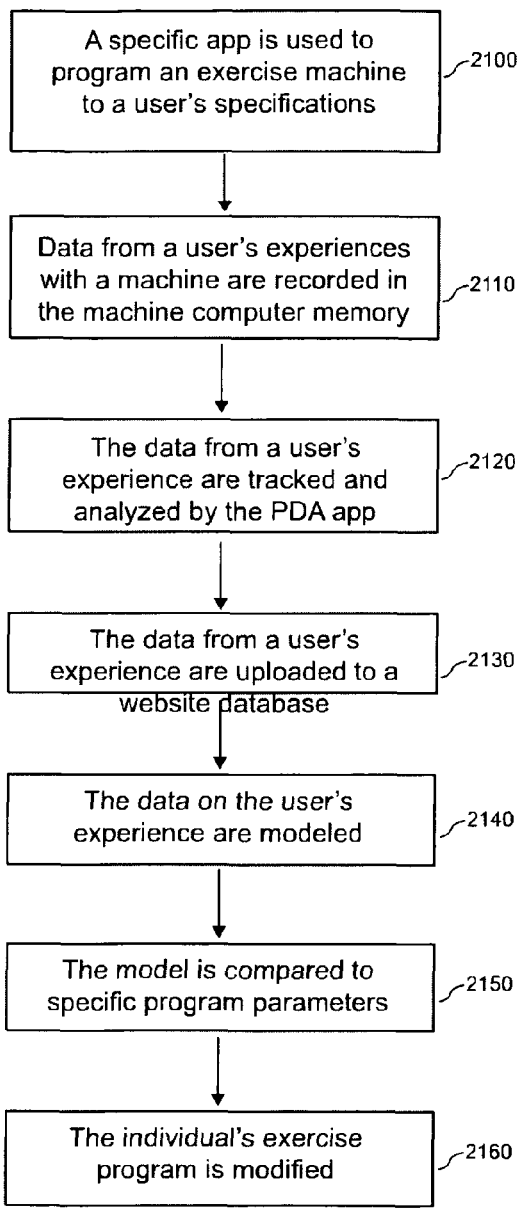
FIG. 21 is a flow chart showing the use of data from a user's experience to improve the exercise regimen.

FIG. 21 shows the use of data from a user's experience to improve the exercise regimen. After a specific app is used to program an exercise machine to a user's specifications (2100), data from a user's experience with a machine are recorded in the machine computer memory (2110). The data from a user's experience are tracked and analyzed by the PDA app (2120) and are uploaded to a Web site database (2130).

The data on the user's experience are modeled (2140) and the model is compared to specific program parameters (2150). The individual's exercise program is then modified (2160).

Figure 22:
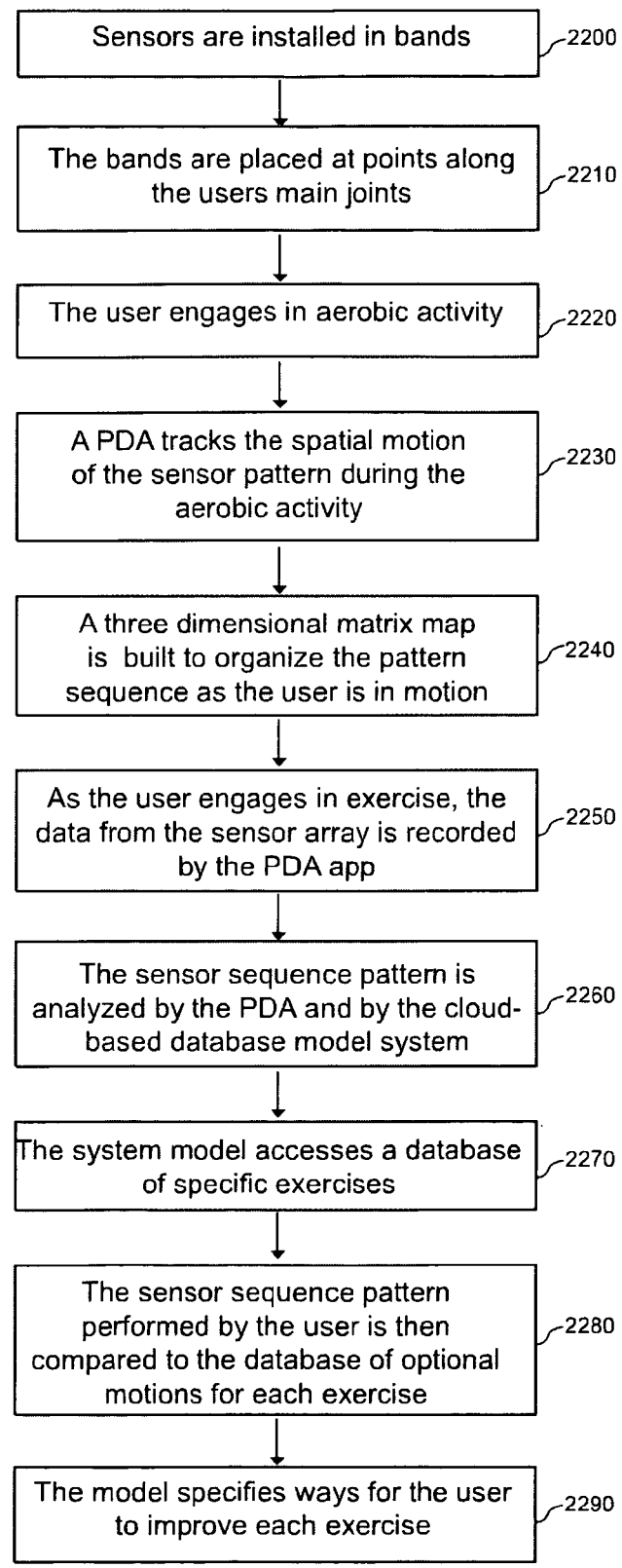
FIG. 22 is a flow chart showing the process of using sensors in user bands to track and optimize a user workout.

FIG. 22 shows the process of using sensors in user bands to track and optimize a user workout. After sensors are installed in bands (2200), the bands are placed at points along the user's main joints (2210) and the user engages in aerobic activity (2220). A PDA tracks the spatial motion of the sensor pattern during the aerobic activity (2230) and a three dimensional map is built to organize the pattern sequence as the user is in motion (2240). As the user engages in exercise, the data from the sensor array is recorded by the PDA app (2250) and the sensor sequence pattern is analyzed by the PDA and by the cloud-based database model system (2260). The system model accesses a database of specific exercises (2270). The sensor sequence pattern performed by the user is then compared to the database of optimal motions for each exercise (2280) and the model specifies ways for the user to improve each exercise (2290).

Figure 23:
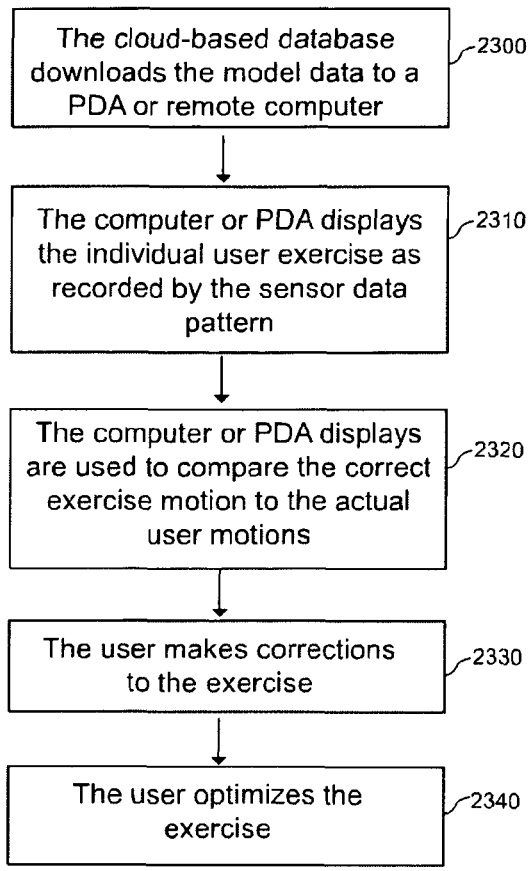
FIG. 23 is a flow chart showing the process of analyzing a workout to provide recommendations to optimize a workout.

FIG. 23 shows the process of analyzing a work out to provide recommendations to optimize a workout. After the cloud-based database downloads the model data to a PDA or remote computer (2300), the computer or PDA displays the individual user exercise as recorded by the sensor data pattern (2310). The computer or PDA displays are used to compare the correct exercise motion to the actual user motion (2320) and the user makes corrections to the exercise (2330) so as to allow the user to optimize the exercise (2340). Once the user makes corrections to the exercise, the process repeats until the exercise is optimized.

Figure 24:
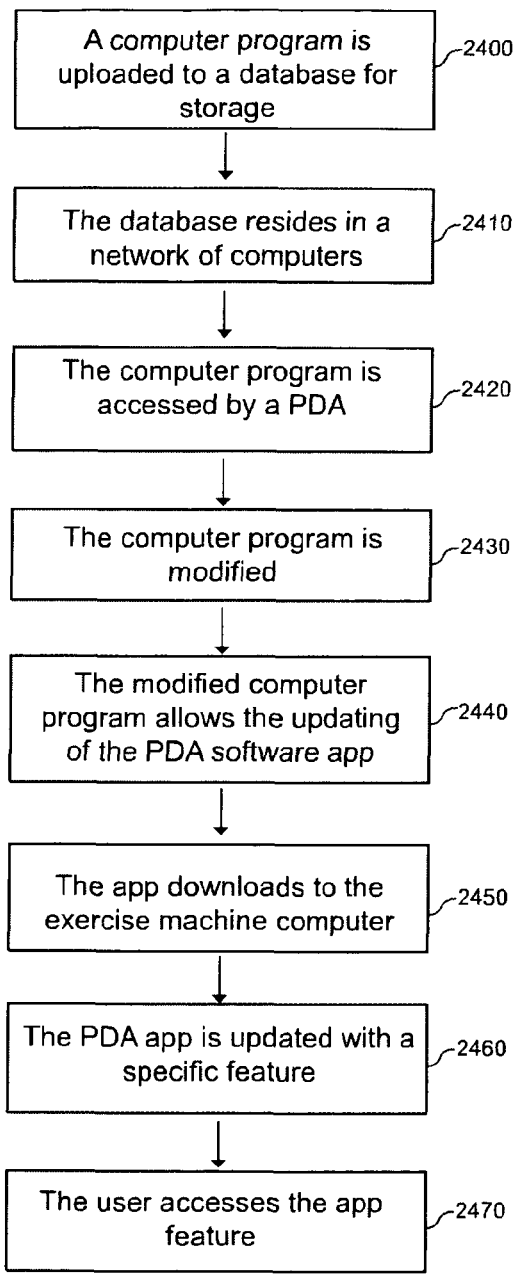
FIG. 24 is a flow chart showing the process of modifying and updating an app for use with a user's workout.

FIG. 24 shows the process of modifying and updating an app for use with a user's workout. After a computer program is uploaded to a database for storage (2400), the database resides in a network of computers (2410). The computer program is accessed by a PDA (2420) and the computer program is modified (2430). The modified computer program allows the updating of the PDA software app (2440) and the app downloads to the exercise machine computer (2450). The PDA app is updated with a specific feature (2460) and the user accesses the app feature (2470).

Figure 25:
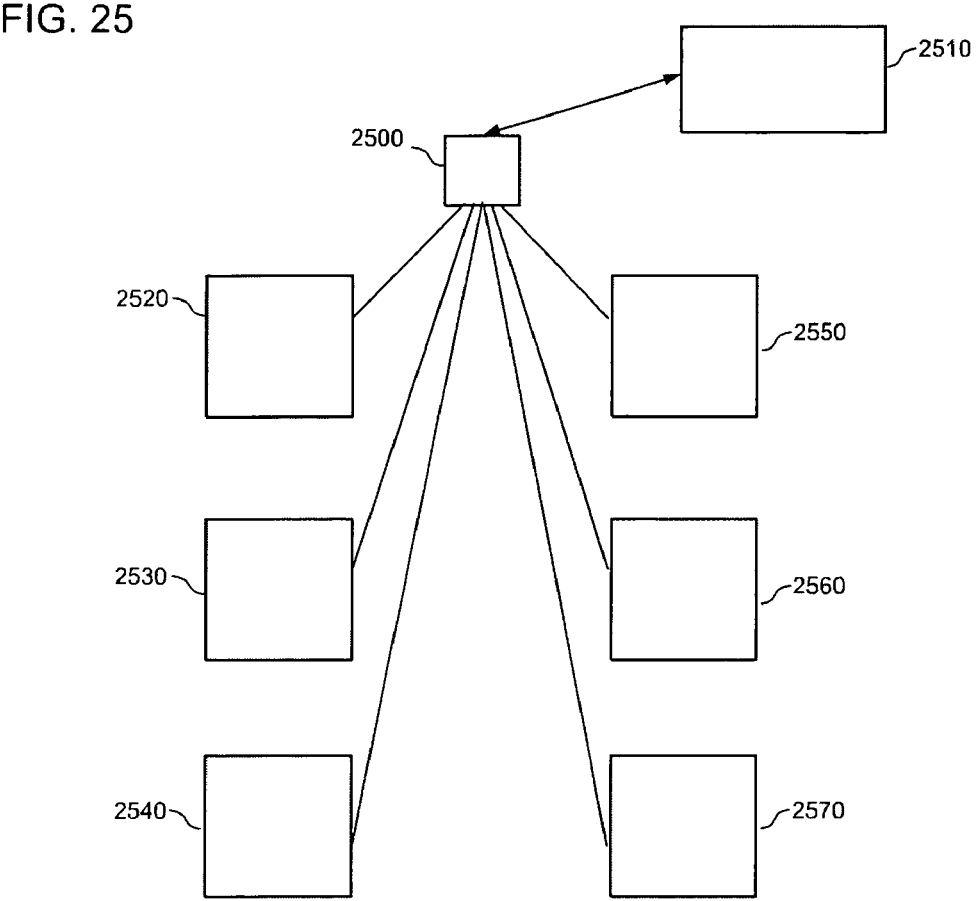
FIG. 25 is a schematic drawing showing how a cloud downloads a program to a PDA and the PDA interacts with six exercise machines.

FIG. 25 shows how a cloud (2510) downloads a program to a PDA (2500) and the PDA interacts with six exercise machines (2520, 2530, 2540, 2550, 2560 and 2570). This example is illustrative only and the system may use one exercise machine or dozens of exercise machines in a network of devices.

Figure 26:
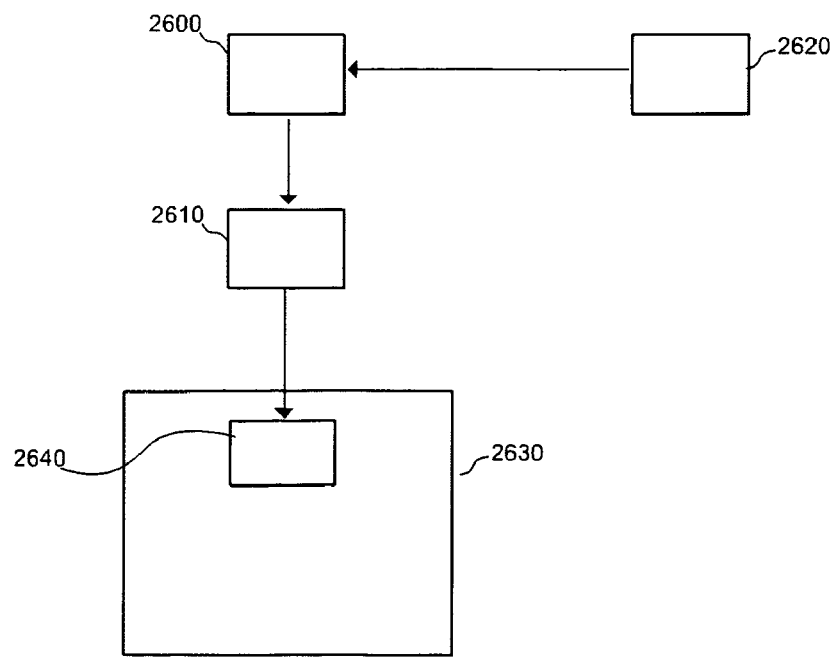
FIG. 26 is a schematic drawing showing the process of updating a third-party web-based program which is downloaded to a PDA and exercise machine.

FIG. 26 shows the process of updating a third-party web-based program which is downloaded to a PDA and exercise machine. The exercise machine (2630) receives a software program (2610) to its computer (2640) sent from a PDA (2610). The software program is sent from a Web based database (2620) to a computer (2600) and then sent to the PDA.

Figure 27:
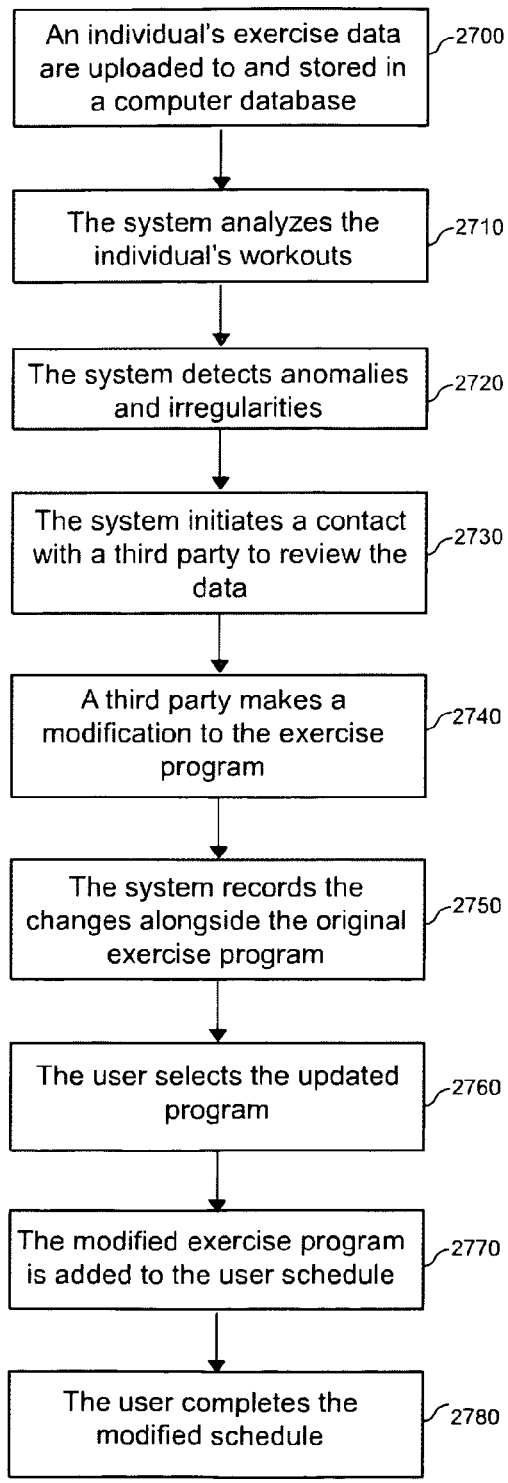
FIG. 27 is a flow chart showing the process of assessing and modifying a workout by a third party.

FIG. 27 shows the process of assessing and modifying a workout by a third party. After an individual's exercise data are uploaded to and stored in a computer database (2700), the system analyzes the individual's workouts (2710). The system detects anomalies and irregularities (2720) and initiates a contact with a third party to review the data (2730). A third party makes a modification to the exercise program (2740) and the system records the changes alongside the original exercise program (2750). The user selects the updated program (2760) and the modified exercise program is added to the user schedule (2770). The user then completes the modified schedule (2780).

Figure 28:
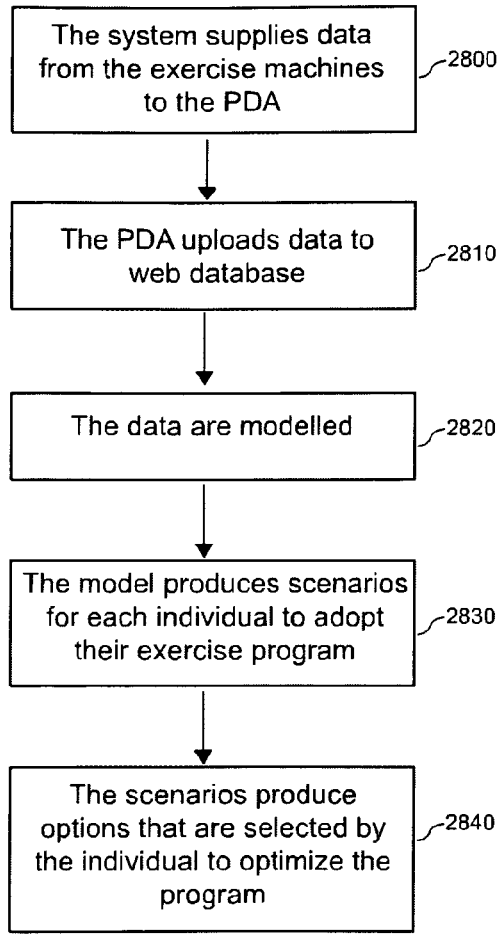
FIG. 28 is a flow chart showing the process of modeling data on a user exercise experience.

FIG. 28 shows the process of modeling data on a user exercise experience. Once the system supplies data from the exercise machines to the PDA (2800), the PDA uploads data to a Web database (2810). The data are then modeled (2820) and the model produces scenarios for each individual to adapt their exercise program (2830). The scenarios produce options that are selected by the individual to optimize the program (2840).

FIG. 29 shows the process of using a diet program that actively tracks an individual's diet with a PDA. After the system collects data on an individual's profile and goals (2900), the system supplies a diet program based on preferences (2910). The diet program app is transferred to the PDA (2920) and the PDA tracks the diet options and schedule (2930). The diet program lists specific food options at specific times (2940), the individual lists what is eaten and when it is eaten (2950), the diet app records the data in the PDA and the PDA uploads the data to a Web database (2960). The individual's diet program is modeled (2970) and the model recommends adjustments to the diet program and recalibrates the schedule (2980).

FIG. 30 shows the process of interaction with an exercise machine to refine a user's workout. After the system is programmed to maintain a user's heart rate at a specified level for a period of time (3000), the system downloads the program to the exercise machine to maintain a specific heart rate (3010). The system uses feedback from the exercise machine to calculate the activity to keep the heart rate at a specific level (3020) and the exercise machine changes settings to keep the heart rate stable until the goal is met (3030).

Figure 31:
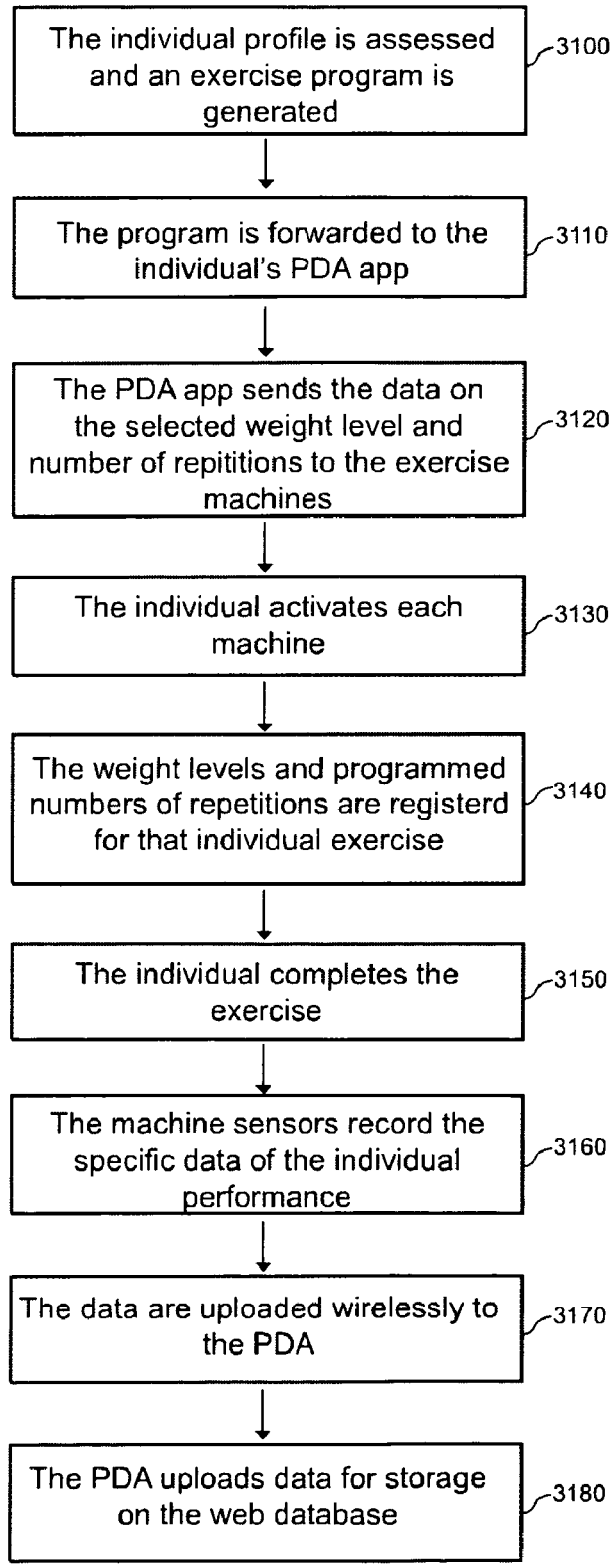
FIG. 31 is a flow chart showing the process of using a PDA app in a user's workout.

FIG. 31 shows the process of using a PDA app in user's workout. Once the individual profile is assessed and an exercise program is generated (3100), the program is forwarded to the individual's PDA app (3110). The PDA app then sends the data on the selected weight level and number of repetitions to the exercise machine (3120). The individual activates each machine (3130) and the weight levels and programmed number of repetitions are registered for that individual exercise (3140). The individual completes the exercise (3150) and the machine sensors record the specific data of the individual performance (3160). The data are then uploaded wirelessly to the PDA (3170) and the PDA uploads data for storage on the Web database (3180).

I claim:

1. A system to manage a reprogrammable exercise machine, comprised of:
    a physical fitness machine used for exercise, including a sensor system;
    a video display integrated in the exercise machine configured to display data from the exercise machine computer and to receive data inputs;
    a computer in the exercise machine, including a database and a means to process and store program code:
    wherein the user selects a specific program configuration of the exercise machine by interacting with the exercise machine display;
    wherein a signal is transmitted from the machine display to the computer in the exercise machine that the user seeks to use a specific configuration of the machine;
    wherein program code is organized in the exercise machine computer to activate a specific program application;
    wherein the program application settings of the exercise machine are automatically modified to activate a specific program function;
    wherein the user uses the exercise machine and activates the program function; and
    wherein the performance of the user is tracked by sensors and recorded and stored in the exercise machine computer memory.

2. The system of claim 1, wherein:
a the user selects a customized software program by accessing the display of the exercise machine;
the display sends a signal to the exercise machine computer to activate the customized program application;
the exercise machine program is modified and the customized program application activates a specific program function; and
the user activates the program function of the exercise machine.

3. The system of claim 1 wherein:
the exercise machine computer analyzes the user performance of the specific program application;
the exercise machine computer uses the analysis to recommend at least one specific change to the program application based on user selected preferences;
the user selects and applies the at least one specific program change; and
the updated program application is applied to subsequent user exercise on the exercise machine.

4. A system to manage a reprogrammable exercise machine, comprised of:
a physical fitness machine used for exercise, including a sensor system;
a computer in the exercise machine, including a machine video display and computer memory;
a software system to manage the functions of the exercise machine;
a user personal digital assistant (PDA) to store and access program applications and configured to wirelessly send signals to and receive signals from the exercise machine computer;
wherein the individual selects an initial program setting by accessing the machine video display or PDA;
wherein the user activates the PDA to wirelessly download a specific program application to the exercise machine computer;
wherein the exercise machine computer accesses the software system to initiate the specific program application;
wherein the exercise machine settings are reset to the specific program application settings;
wherein the individual using the exercise machine engages in a specific activity using the undated program application settings; and
wherein the performance of the user is tracked by sensors and recorded and stored in the exercise machine computer memory.

5. The system of claim 4, wherein:
a wireless signal is sent from the exercise machine computer to the PDA;
the user performance of using the most recent program application is recorded in the PDA memory;
the PDA performs an analysis of the user performance; and
the data on the user's performance experience are modeled.

6. The system of claim 4 wherein:
the exercise machine is a cardio device including an elliptical machine, a bicycle, a stair-master or a treadmill machine.

7. The system of claim 4, wherein:
the exercise machine is a weight training machine.

8. The system of claim 4, wherein:
the PDA is a tablet computer, laptop computer or a smart phone.

9. The system of claim 4, wherein:
the exercise machine computer sends a wireless signal to the user PDA;
the performance of the user on the exercise machine is stored in the PDA memory:
the PDA analyzes the user performance data; and
the analysis is displayed on the PDA display.

10. The system of claim 5, wherein;
the model is compared to specific program parameters;
the individual's exercise program is modified by the PDA by applying the model; and
the updated program is used in subsequent applications.

11. A system to manage an automated a reprogrammable exercise machine, comprised of;
a physical fitness machine used for exercise, including a sensor system;
a computer in the exercise machine, including a machine video display;
a software system to manage the functions of the exercise machine, including data storage:
a user personal digital assistant (PDA) to store and access program applications and configured to wirelessly send signals to and receive signals from the exercise machine computer;
wherein the PDA wirelessly sends a software application to the exercise machine when activated by the user:
wherein the software application activates a specific function in the computer of the exercise machine to reprogram the settings of the exercise machine;
wherein the exercise machine changes its settings to conform to the updated program application;
wherein the user uses the exercise machine at the updated specific program settings;
wherein the user updates the program application for each use based on an analysis of prior exercises;
wherein the performance of the user is tracked by sensors and recorded and stored in the exercise machine computer memory; and
wherein when the program application is updated and reprogrammed for the user for each use, the user uses the exercise machine with the most recent updated program settings.

12. The system of claim 11, wherein:
the exercise machine computer sends a wireless signal to the user PDA when activated by the user;
the performance of the user on the exercise machine is recorded in the PDA;
the PDA analyzes the performance of the user performance; and
the PDA develops an optimized exercise program for the user based on an analysis of at least two prior user performances from data on past performances stored in a database.

13. The system of claim 11, wherein:
the exercise machine computer sends a signal with data on the user's exercise performance experience to a website database; and
the data on the user's experience are modeled.

14. The system of claim 13, wherein:
the model is compared to specific program parameters; the individual's exercise program is modified;
the modified program is downloaded to the exercise machine;

the modified program application is activated in the exercise machine; and the user uses the exercise machine with the modified program application functions.

15. The system of claim 11, wherein:

the exercise machine is a cardio device including an elliptical machine, a bicycle, a stair-master or a treadmill machine.

16. The system of claim 11, wherein:

the exercise machine is a weight training machine.

17. The system of claim 11, wherein:

the PDA is a tablet computer, laptop computer or a smart phone.

18. The system of claim 13, wherein:

a web-based computer model aggregates data on the exercise performance of at least two users:

the web-based computer generates an optimal program application for specific users from the multiple user model analyses;

the user uses the PDA to select a specific program application from the web site to implement in an exercise machine:

the selected program application is downloaded to the exercise machine;

the user uses the exercise machine with the modified program application functions.

* * * * *